United States Patent
Euliano, II et al.

(10) Patent No.: US 9,351,682 B2
(45) Date of Patent: *May 31, 2016

(54) SENSOR INTERFACE SYSTEM

(75) Inventors: Neil Russell Euliano, II, Gainesville, FL (US); Dorothee Marossero, Coogee (AU); Shalom Darmanjian, Gainesville, FL (US); Daniel Patrick McKenna, Gainesville, FL (US)

(73) Assignee: Convergent Engineering, Inc., Newberry, FL (US)

( * ) Notice: Subject to any disclaimer, the term of this patent is extended or adjusted under 35 U.S.C. 154(b) by 890 days.

This patent is subject to a terminal disclaimer.

(21) Appl. No.: 13/292,787

(22) Filed: Nov. 9, 2011

(65) Prior Publication Data

US 2012/0071744 A1 Mar. 22, 2012

Related U.S. Application Data

(63) Continuation-in-part of application No. 12/941,614, filed on Nov. 8, 2010, which is a continuation of application No. 11/582,714, filed on Oct. 18, 2006, now Pat. No. 7,828,753.

(60) Provisional application No. 61/411,702, filed on Nov. 9, 2010.

(51) Int. Cl.
*A61B 5/0444* (2006.01)
*A61B 5/00* (2006.01)
(Continued)

(52) U.S. Cl.
CPC .............. *A61B 5/4362* (2013.01); *A61B 5/033* (2013.01); *A61B 5/4356* (2013.01); *A61B 5/0011* (2013.01);
(Continued)

(58) Field of Classification Search
CPC ............. A61B 5/0011; A61B 5/02411; A61B 5/04028; A61B 5/0448; A61B 5/4343–5/4362; A61B 5/72; A61B 5/7278
USPC .................. 600/304, 376, 382, 511, 588, 591
See application file for complete search history.

(56) References Cited

U.S. PATENT DOCUMENTS 3,703,168 A 11/1972 Frink
4,256,118 A 3/1981 Nagel
(Continued)

FOREIGN PATENT DOCUMENTS

WO WO 86/02250 4/1986
WO WO 2003/028550 4/2003
(Continued)

OTHER PUBLICATIONS

Garfield et al., "Comparing uterine electromyography activity of antepartum patients versus term labor patients," *American Journal of Obstetrics and Gynecology*, Jul. 2005, pp. 23-29, vol. 193, No. 1.
(Continued)

*Primary Examiner* — Lee S Cohen
*Assistant Examiner* — Erin M Cardinal
(74) *Attorney, Agent, or Firm* — Finnegan, Henderson, Farabow, Garrett & Dunner, LLP

(57) ABSTRACT

A sensor interface system for providing a connection between at least one sensor and a maternal-fetal monitor, wherein the interface system converts electrical muscle activity captured by the sensor(s) into uterine activity data signals for use by the maternal-fetal monitor. The sensor interface system of the invention preferably includes a conversion means for converting the signals from the sensor(s) into signals similar to those produced by a tocodynamometer.

20 Claims, 21 Drawing Sheets

(51) Int. Cl.
*A61B 5/03* (2006.01)
*A61B 5/024* (2006.01)
*A61B 5/0448* (2006.01)

(52) U.S. Cl.
CPC ........... *A61B 5/02411* (2013.01); *A61B 5/0444* (2013.01); *A61B 5/0448* (2013.01); *A61B 2560/045* (2013.01)

(56) References Cited

U.S. PATENT DOCUMENTS

| | | | |
|---|---|---|---|
| 4,781,200 A | 11/1988 | Baker | |
| 4,967,761 A | 11/1990 | Nathanielsz | |
| 4,987,898 A | 1/1991 | Sones | |
| 5,301,680 A | 4/1994 | Rosenberg | |
| 5,373,852 A | 12/1994 | Harrison et al. | |
| 5,397,344 A | 3/1995 | Garfield et al. | |
| 5,442,940 A | 8/1995 | Secker et al. | |
| 5,483,967 A * | 1/1996 | Ohtake | 600/508 |
| 5,483,970 A | 1/1996 | Rosenberg | |
| 5,546,953 A | 8/1996 | Garfield | |
| 5,623,939 A | 4/1997 | Garfield | |
| 5,634,476 A * | 6/1997 | Orkin et al. | 600/588 |
| 5,671,749 A | 9/1997 | Hon | |
| 5,776,073 A | 7/1998 | Garfield et al. | |
| 5,785,664 A | 7/1998 | Rosenberg | |
| 5,865,733 A * | 2/1999 | Malinouskas et al. | 600/300 |
| 6,421,558 B1 | 7/2002 | Huey et al. | |
| 6,663,570 B2 | 12/2003 | Mott et al. | |
| 6,694,192 B2 | 2/2004 | Policker et al. | |
| 6,751,498 B1 | 6/2004 | Greenberg et al. | |
| 6,816,744 B2 | 11/2004 | Garfield et al. | |
| 6,823,211 B2 | 11/2004 | Simpson et al. | |
| 6,879,858 B1 | 4/2005 | Adams | |
| 6,898,460 B2 | 5/2005 | Hoctor et al. | |
| 7,761,698 B2 | 7/2010 | Ichtertz | |
| 7,831,302 B2 | 11/2010 | Thomas | |
| 2002/0010494 A1 | 1/2002 | Policker et al. | |
| 2002/0193670 A1 | 12/2002 | Garfield et al. | |
| 2002/0193701 A1 | 12/2002 | Simpson et al. | |
| 2003/0135130 A1 | 7/2003 | Hoctor et al. | |
| 2004/0243015 A1 * | 12/2004 | Smith et al. | 600/511 |
| 2005/0105644 A1 | 5/2005 | Baxter et al. | |
| 2005/0267376 A1 | 12/2005 | Marossero et al. | |
| 2005/0267377 A1 * | 12/2005 | Marossero et al. | 600/511 |
| 2006/0149168 A1 | 7/2006 | Czarnek | |
| 2007/0191728 A1 * | 8/2007 | Shennib | 600/546 |
| 2007/0260133 A1 | 11/2007 | Meyer | |
| 2008/0082024 A1 | 4/2008 | Meyer et al. | |
| 2008/0154110 A1 * | 6/2008 | Burnes et al. | 600/382 |
| 2008/0177168 A1 * | 7/2008 | Callahan et al. | 600/382 |

FOREIGN PATENT DOCUMENTS

| | | |
|---|---|---|
| WO | WO 2004/084087 | 9/2004 |
| WO | WO 2005/052848 | 6/2005 |

OTHER PUBLICATIONS

Garfield et al., "Use of uterine EMG and cervical LIF in monitoring pregnant patients," *BJOG: an International Journal of Obstetrics and Gynecology*, Mar. 2005, pp. 103-108, vol. 112, Suppl. 1.

Garfield et al., "Uterine Electromyography and Light-Induced Fluorescence in the Management of Term and Preterm Labor," *J Soc Gynecol Investig*, Sep.-Oct. 2002, pp. 265-275, vol. 9, No. 5.

Khalil et al., "Uterine EMG Analysis: A Dynamic Approach for Change Detection and Classification," *IEEE Transactions on Biomedical Engineering*, Jun. 2000, pp. 748-756, vol. 47, No. 6.

Leman et al., "Use of the Electrohysterogram Signal Characterization of Contractions During Pregnancy," *IEEE Transactions on Biomedical Engineering*, Oct. 1999, pp. 1222-1229, vol. 46, No. 10.

Marque et al., "Uterine EHG Processing for Obstetrical Monitoring," *IEEE Transactions on Biomedical Engineering*, Dec. 1986, pp. 1182-1186, vol. BME-33, No. 12.

Shafik, "Electrohysterogram: Study of the electromechanical activity of the uterus in humans," *European Journal of Obstetrics & Gynecology and Reproductive Biology*, May 1997, pp. 85-89, vol. 73, No. 1.

Verdenik et al., "Uterine electrical activity as predictor of preterm birth in women with preterm contractions," *European Journal of Obstetrics & Gynecology and Reproductive Biology*, Apr. 2001, pp. 149-153, vol. 95, No. 2.

* cited by examiner

SENSOR INTERFACE SYSTEM

CROSS-REFERENCE TO A RELATED APPLICATION

This application is a continuation-in-part application of U.S. application Ser. No. 12/941,614, filed Nov. 8, 2010, which is a continuation application of U.S. Ser. No. 11/582,714, filed Oct. 18, 2006, now U.S. Pat. No. 7,828,753, both of which are incorporated herein by reference in their entireties. Also, this application claims the benefit of U.S. provisional application Ser. No. 61/411,702, filed Nov. 9, 2010, which is incorporated herein by reference in its entirety.

BACKGROUND OF INVENTION

Assessment of the fetus during pregnancy, and particularly during labor and delivery, is an essential yet elusive goal. While most patients will deliver a healthy child with or without monitoring, more than 5 out of every 1,000 deliveries of a viable fetus near term are stillborn, with half having an undetermined cause of death. (National Vital Statistics System (NVSS), CDC, NCHS as published in "Healthy People 2010, Understanding and Improving Health: Chapter 16," co-authored by the Centers for Disease Control and Prevention and Health Resources and Services Administration, $2^{nd}$ Edition, U.S. Government Printing Office, November 2000). The risk of this unfortunate consequence is increased in a subgroup of "high risk" patients (e.g., diabetics). In addition to regular obstetric observation, after 23 weeks gestation antepartum ("in utero") fetal monitoring consists of the following (in order of complexity):
  1. maternal report of fetal movement;
  2. non-stress test (NST)—monitor fetal heart rate (FHR) by ultrasound, looking for baseline rate, variability and presence of accelerations above the baseline;
  3. contraction stress test (CST)—response of the FHR to uterine contractions, either natural or induced; and
  4. biophysical profile (BPP)—NST plus ultrasonographic evaluation of fetal movements and amniotic fluid volume.

Despite their wide acceptance, these tests offer limited predictive value, and give only a glimpse of the fetus at the time of testing. For high risk patients, once or twice weekly surveillance is often indicated, entailing both expense and inconvenience for the patient.

Intrapartum fetal surveillance is accomplished routinely with intermittent auscultation or continuous Doppler monitoring of the FHR, together with palpation or tocodynamometry (strain gauge) monitoring of contractions. When indicated, more invasive monitors are available, but require ruptured membranes/adequate cervical dilation, and entail some risk, primarily infectious. These monitors include, without limitation:
  1. fetal scalp electrode—a wire electrode inserted into the fetal scalp;
  2. intra-uterine pressure catheter (IUPC)—enables quantitative measurement of contractions; and
  3. fetal scalp sampling—a blood sample drawn for pH analysis.

Contraction detection allows monitoring of the progress of labor. A device commonly used in monitoring contractions is the tocodynamometer. The tocodynamometer detects physical changes in the curvature of the mother's abdomen (usually with a strap or belt that is placed about the abdomen) during a contraction and translates these changes into a printed curve. The tocodynamometer detects only the presence or absence of tension on the abdomen (whether from uterine contraction or maternal movement), and often fails in the presence of obesity. Unfortunately, patients are recommended to remain in a supine position when using a tocodynamometer to monitor labor, which has been found to be the least effective physiological position for encouraging fetal internal rotation and often causes maternal hypotension and discomfort.

When cervical dilation lags behind the anticipated labor curve, oxytocin is often indicated to induce a more effective contraction pattern. Safe titration of the oxytocin may require accurate determination of "montevideo units" which measure the strength of uterine contractions over 10 minutes. This requires the more invasive IUPC, a catheter placed into the uterus, alongside the fetus, to measure the pressure generated by uterine contractions.

The rationale for use of intrapartum electronic fetal monitoring (EFM) assumes that FHR abnormalities accurately reflect hypoxia (inadequate oxygen to the fetus), and that early recognition of this could induce intervention to improve outcome for both mother and fetus. Unfortunately, numerous studies have failed to identify this improved outcome with the use of EFM in low-risk deliveries. In fact some studies have actually shown an increase in morbidity from a higher operative delivery rate. Perhaps this should not be surprising in light of the variability in interpretation of FHR tracings and their lack of specificity for hypoxia. Yet, continuous EFM remains the standard of care in US hospitals, in large part due to medical and legal concerns.

Recently, analysis of the fetal ECG (electrocardiogram) has held promise, with some features of the waveform more specifically indicating fetal hypoxia. Use of the waveform analysis reduced the incidence of severe metabolic acidosis at birth, while necessitating fewer scalp samples and operative deliveries. Unfortunately, acquisition of the FECG was through the fetal scalp electrode described above which is both invasive and limited in its application. The necessity for access to the fetal scalp requires both adequate cervical dilation and ruptured membranes, eliminating this procedure for antepartum fetal surveillance, as well as early labor.

Non-invasive acquisition of the FECG is a recognized issue of mixed signals. Electrodes placed on the skin surface will record all transmitted electrical activity including maternal ECG, maternal skeletal muscle, uterine muscle, fetal skeletal muscle, and fetal ECG. To address the inadequacies noted above, various methods have been proposed for use in processing maternal abdominal signals to provide more accurate FECG extraction. These methods include subtractive filtering (see, for example, U.S. Pat. No. 4,945,917), adaptive filtering (see, for example, Widrow, B. et al., "Adaptive Noise Canceling: Principals and Applications," *Proc. IEEE,* 63(12):1692-1716 (December 1975); Adam, D. and D. Shavit, "Complete Fetal ECG Morphology Recording by Synchronized Adaptive Filtration," *Med. & Biol. Eng. & Comput.,* 28:287-292 (July 1990); Ferrara, E. and B. Widrow, "Fetal Electrocardiogram Enhancement by Time Sequenced Adaptive Filtering," *IEEE Trans. Biomed. Eng.,* BME-29(6):458-460 (June 1982); U.S. Pat. Nos. 4,781,200 and 5,042,499), orthogonal basis (Longini, R. et al., "Near Orthogonal Basis Function: A Real Time Fetal ECG Technique," *IEEE Trans. On Biomedical Eng.,* BME-24(1):39-43 (January 1977); U.S. Pat. No. 5,042,499), linear combination (Bergveld, P. et al., "Real Time Fetal ECG Recording," *IEEE Trans. On Beiomedical Eng.,* BME-33(5):505-509 (May 1986)), single value decomposition (Callaerts, D. et al., "Comparison of SVD Methods to Extract the Fetal Electrocardiogram from Cutaneous Electrodes Signals," *Med. & Biol. Eng. & Comput.,* 28:217-224

(May 1990); U.S. Pat. No. 5,209,237), and MECG averaging and correlation (Abboud, S. et al., "Quantification of the Fetal Electrocardiogram Using Averaging Technique," *Comput. Biol. Med.*, 20:147-155 (February 1990); Cerutti, S. et al., "Variability Analysis of Fetal Heart Rate Signals as Obtained from Abdominal Electrocardiographic Recordings," *J. Perinat. Med.*, 14:445-452 (1986); J. Nagel, "Progresses in Fetal Monitoring by Improved Data Acquisition," *IEEE Eng. Med. & Biol. Mag.*, 9-13 (September 1984); Oostendorp, T. et al., "The Potential Distribution Generated by Fetal Heart at the Maternal Abdomen," *J. Perinat. Med.*, 14:435-444 (1986); U.S. Pat. No. 5,490,515). These methods, unfortunately, do not reliably enable continuous extraction of maternal-fetal data or cannot capture a comprehensive account of maternal-fetal health based on a combination of test results (i.e., fetal heart rate, fetal ECG, maternal ECG, and maternal uterine activity (EHG)).

Recently, magnetocardiography has been utilized in extracting fetal ECG (see, for example. Sturm, R. et al., "Multi-channel magnetocardiography for detecting beat morphology variations in fetal arrhythmias," *Prenat Diagn.* 24(1):1-9 (January 2004); and Stinstra, J. et "Multicentre study of fetal cardiac time intervals using magnetocardiography," *BJOG*, 109(11):1235-43 (November 2002)). Unfortunately, magnetocardiography is limited in application, technologically complex, and difficult to administer to assess accurate fetal ECG readings.

Uterine contractions are the result of the coordinated actions of individual myometrial cells. At the cellular level, the contractions are triggered by a voltage signal called an action potential. During pregnancy, cellular electrical connectivity increases such that the action potential propagates to produce a coordinated contraction involving the entire uterus. The action potential during a uterine contraction can be measured with electrodes placed on the maternal abdomen resulting in a uterine EMG signal (hereinafter referred to as "EHG": electrohysterogram). Specifically, the EHG signal can be processed to produce a signal that is similar to the standard uterine activity signal from the tocodynamometer or IUPC. The EHG provides contraction frequency and duration information. To date, EHG signals have not been used in assessing the intra-uterine pressure or predicting montevideo units.

Postpartum, continuous uterine contraction is required to minimize uterine bleeding from the placental detachment site. Hemorrhage is the leading cause of peripartum maternal death, and most of these are postpartum hemorrhage due to this "uterine atony." Current monitoring consists of serial uterine palpation at intervals of several hours. Diagnosis is usually made by patient complaint of severe bleeding, or hypovolemic shock (from hemorrhage). Neither IUPC nor tocodynamometer monitoring is available at this time. The EHG would provide a unique means for monitoring the uterine tone, providing an early warning of atony and potential hemorrhage.

Devices that utilize invasive techniques for monitoring fetal health include those disclosed in U.S. Pat. Nos. 6,594, 515; 6,115,624; 6,058,321; 5,746,212; 5,184,619; 4,951,680; and 4,437,467.

Accordingly, a cost-effective, more reliable system and method for non-invasively measuring uterine activity, in particular contractions during labor, without the need for expensive equipment replacement would be beneficial. Also, a cost-effective sensor and/or monitoring system for both the mother and fetus that can continuously monitor, in real-time, and accurately extract and evaluate maternal/fetal heart rates and ECGs, and maternal EHG, without the need for expensive equipment replacement, would be beneficial.

BRIEF SUMMARY OF THE INVENTION

Without limitation, the term sensor refers to either an acoustic sensor such as a microphone, an electric sensor such as an electrode, or any number of other types of sensors useful in extracting maternal-fetal information. The present invention provides a unique interface system that converts sensor signals containing information of the maternal and fetal heart rate and ECG, and maternal muscle activity captured by non-standard sensors (such as for ECG electrodes and acoustic sensors) into signals that provide inputs of uterine activity and heart rate and ECG to a maternal-fetal monitor without the use of existing sensors. As used herein, the term "existing sensor" refers to an intra-uterine pressure catheter (IUPC) sensor, a tocodynamometer sensor, a fetal scalp electrode sensor, or an ultrasound sensor. For example, existing sensors are generally the sensors that are typically used with the maternal-fetal monitor and/or the sensors provided or sold with the maternal-fetal monitor. As used herein, the term "non-standard sensor" refers to a sensor that is not an IUPC sensor, a tocodynamometer sensor, a fetal scalp electrode sensor, or an ultrasound sensor. These "standard" sensors are typically used with maternal-fetal monitors, but, in an embodiment, the subject invention can convert sensor signals captured by non-standard sensors into signals that provide inputs of uterine activity and heart rate and ECG to a maternal-fetal monitor without the use of existing sensors.

The present invention provides a unique interface system that converts electrical muscle activity captured by common electrodes (such as for ECG/EMG) into signals that provide uterine activity data to a maternal-fetal monitor without the use of a tocodynamometer.

Preferably, the interface system comprises a cable that converts output from electrodes or sensors to an output comparable to those provided by a tocodynamometer, IUP, FSE, or ultrasound monitor (collectively PROBE) for connection to a maternal-fetal monitor. The monitor can be configured for a uterine activity sensor (such as a tocodynamometer, an intrauterine pressure catheter, a fetal scalp electrode, and the like).

In one embodiment, the interface system of the invention comprises an interface (also referred to herein as a connector) for at least one electrode, an interface for a compatible port in a maternal-fetal monitor, and a signal converter for converting electrode output provided through the electrode interface to output comparable to those provided by a tocodynamometer.

In one embodiment, the interface system of the invention comprises an interface (also referred to herein as a connector) for at least one sensor, an interface for a compatible port in a maternal-fetal monitor, and a signal converter for converting sensor output provided through the sensor interface to output comparable to those provided by a standard PROBE.

In one embodiment, the interface system comprises a cable portion formed integrally with an electrode interface, a maternal-fetal monitor port interface, and a signal converter to provide a unitary cable structure. In another embodiment, the interface system comprises an electrode interface that includes a wireless signal transmitter, a maternal-fetal monitor port interface, and a signal converter that includes a wireless signal receiver, wherein all of these components are physically independent from each other.

In one embodiment, the interface system comprises a cable portion formed integrally with a sensor interface, a maternal-fetal monitor port interface, and a signal converter to provide a unitary cable structure. In another embodiment, the interface system comprises a sensor interface that includes a wireless signal transmitter, a maternal-fetal monitor port interface, and a signal converter that includes a wireless signal receiver, wherein all of these components are physically independent from each other or combined in different combinations.

In an embodiment, the interface system comprises an electrode interface for multiple electrodes, more preferably between 2 and 6 electrodes. Preferably, the maternal-fetal monitor port interface is operably connectable with a uterine activity port or a tocodynamometer port available on the maternal-fetal monitor.

In a preferred embodiment, the interface system comprises a sensor interface for multiple sensors, more preferably between 2 and 8 sensors. Preferably, the maternal-fetal monitor port interface is operably connectable with one or more ports on the maternal-fetal monitor.

In an embodiment, an interface system can include: a sensor interface for operably connecting to at least one maternal abdominal sensor and receiving at least one signal from the at least one maternal abdominal sensor; a signal converter connected to the sensor interface, wherein the signal converter processes the at least one signal into output data that mimics electrical output from a tocodynamometer, intra-uterine pressure catheter, fetal scalp electrode, and/or ultrasound device; and a maternal-fetal monitor port interface for operably and physically connecting to a maternal-fetal monitor, wherein the maternal abdominal sensor is not a tocodynamometer or an ultrasound sensor.

In an embodiment, a sensor array designed for a maternal abdomen can include: a substrate; at least two sensors on the substrate; and a curved electrical connection connected to each sensor, wherein each curved electrical connection is configured to allow the sensor array to conform to the shape of the maternal abdomen.

In an embodiment, a method of optically coupling a signal converter and a maternal-fetal port, wherein the signal converter comprises an LED circuit, can include: providing an optical interface for the maternal-fetal port, wherein the optical interface comprises an optically-isolated balanced bridge circuit comprising a photo-resistor optically coupled to the LED circuit; driving the LED circuit with a voltage-to-current converter device, thereby modulating a current through the LED circuit and creating a maternal-fetal port input signal; and providing the maternal-fetal port input signal to the maternal-fetal port.

The present invention provides a new and improved interface system that has the ability to provide accurate contraction and cardiac data by converting electrode or sensor signals into PROBE-comparable data that can be processed using commercially available maternal-fetal monitors. The present invention is particularly advantageous because of low costs of manufacture with regard to both materials and labor, which accordingly induces low prices of sales to the consuming public.

Other features and advantages of the invention will be apparent from the following description and accompanying drawings.

DETAILED DISCLOSURE

The present invention provides a unique interface system that converts electrical muscle activity signals captured by at least one electrode into signals that provide uterine activity data to a conventional maternal-fetal monitor without the use of a tocodynamometer or invasive maternal-fetal monitoring device (such as an intra-uterine pressure catheter (IUPC) or fetal scalp electrode). The information provided by the interface system can then be processed by the maternal-fetal monitor to generate information regarding EHG signals, uterine contraction during and after labor, uterine atony, intrauterine pressure, Montevideo units, and the like.

Figure 1:
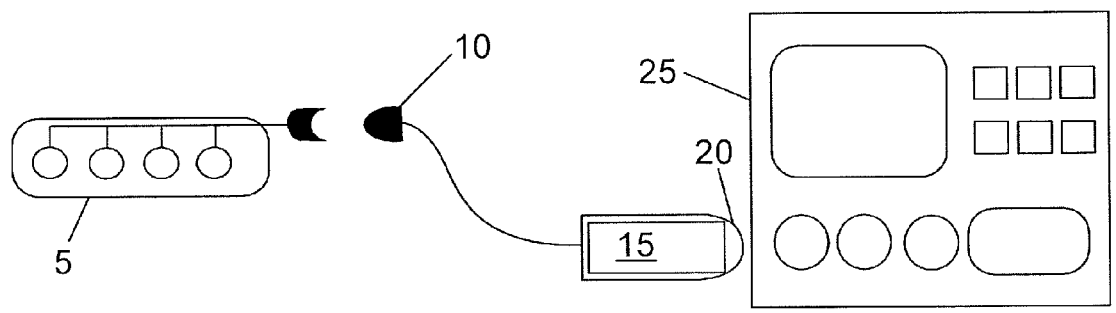
FIG. 1 illustrates one embodiment of the invention wherein an interface cable of the invention is operatively connected to a strip of electrodes or sensors and a maternal-fetal monitor.
Figure 23:
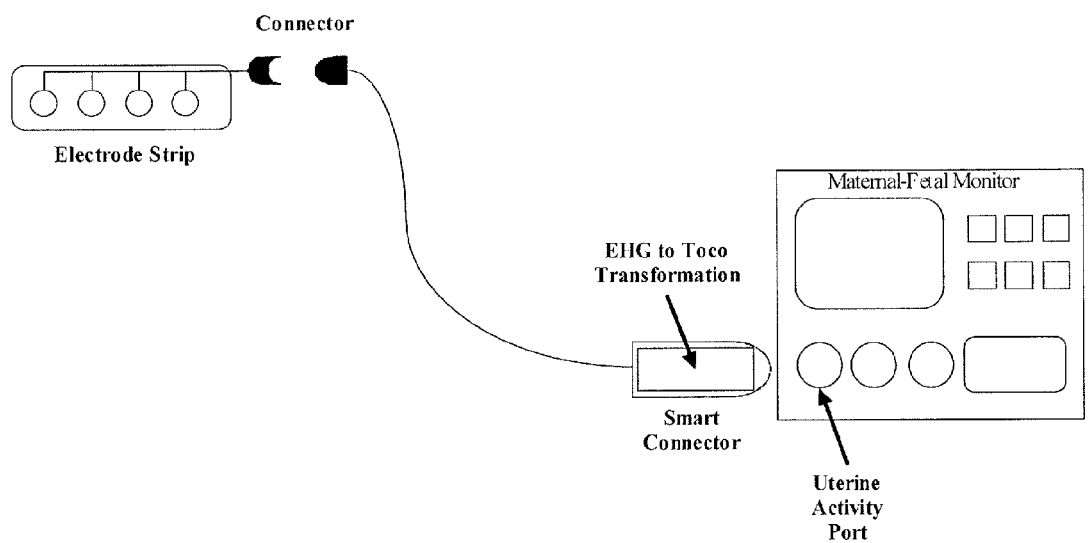
FIG. 23 illustrates one embodiment of the invention wherein an interface cable of the invention is operatively connected to a strip of electrodes or sensors and a maternal-fetal monitor.

In one embodiment, as illustrated in FIGS. 1 and 23, the interface system comprises a cable integrally formed with an electrode interface 10 (or also referred to herein as a connector), a maternal-fetal monitor port interface 20, and a signal converter 15 that converts output signals from electrodes to an output signal comparable to those provided by a tocodynamometer or IUPC. The interface system is preferably in the form of a unitary cable structure. The electrode interface 10 can be connected to any conventional electrode or set of electrodes 5.

The present invention provides a unique interface system that converts signals captured by at least one sensor into signals that provide PROBE data to a conventional maternal-fetal monitor without the use of a standard PROBES (such as an intra-uterine pressure catheter (IUPC), ultrasound (U/S), tocodynamometer (toco) or fetal scalp electrode (FSE)). The information provided by the interface system can then be processed by the maternal-fetal monitor to generate information regarding uterine contraction during and after labor, uterine atony, intrauterine pressure, Montevideo units, fetal heart rate, decelerations, fetal ECG, fetal distress, and the like.

In an embodiment, as illustrated in FIGS. 1 and 23, the interface system comprises a cable integrally formed with a sensor interface 10 (or also referred to herein as a connector), a maternal-fetal monitor port interface 20, and a signal converter 15 that converts output signals from sensors to an output signal comparable to those provided by a PROBE. The interface system is preferably in the form of a unitary cable structure. The sensor interface 10 can be connected to any conventional sensor or set of sensors 5.

The cable can transmit analog, digital, or a combination of analog and digital signals. In certain embodiments, the cable is specifically designed for communication/connection with a conventional maternal-fetal monitor 25. For example, a cable can be preprogrammed with the expected voltage range for the monitor.

Figure 2:
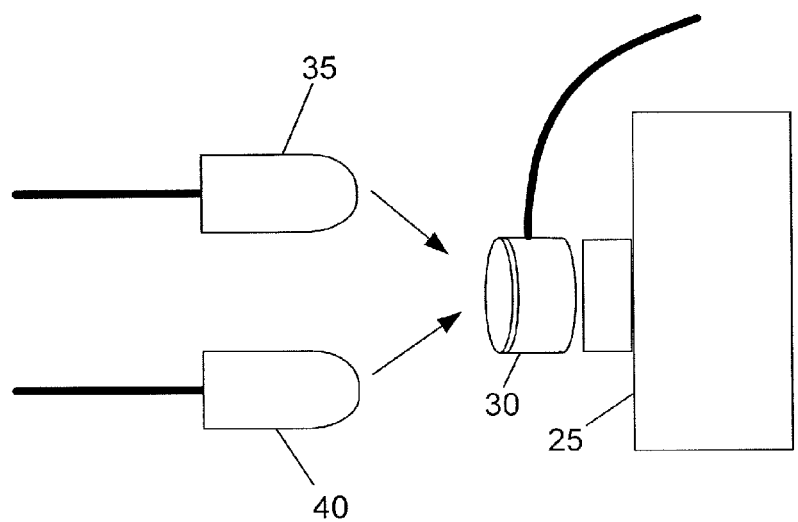
FIG. 2 illustrates a power adapter that can be used in combination with the interface cable of the invention.
Figure 24:
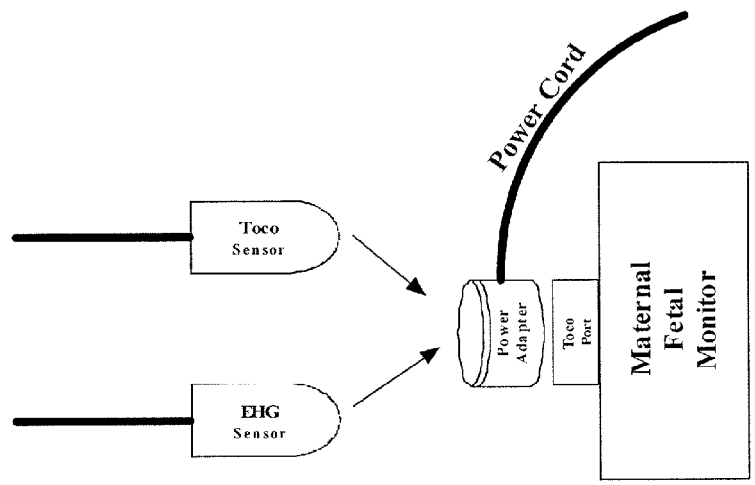
FIG. 24 illustrates a power adapter that can be used in combination with the interface cable of the invention.

In a related embodiment, the cable uses the same power as that supplied by the maternal-fetal monitor, and thus will not require a separate power supply. In certain embodiments, as illustrated in FIGS. 2 and 24, an additional power connector is included in the system that allows for permanent power connectivity. The power connector can be designed as a semi-permanent adapter 30 connected to the maternal-fetal monitor that allows both standard tocodynamometer (or IUPC) cables 35 and an EHG cable 40 to be plugged into it without removing the adapter from the monitor 25. In this way, the power system can be attached to the monitor once and not removed, allowing repeated swapping of the tocodynamometer (or IUPC) cable and the interface system of the present invention without undue hassle.

The electrode interface can be connected to any conventional electrode or set of electrodes including, but not limited to, disposable electrodes (including electrodes that are without gel and pregelled), reusable disc electrodes (including gold, silver, stainless steel, or tin electrodes), headbands, and saline-based electrodes. Contemplated electrodes include those used for monitoring electrocardiography (ECG/EKG); electroencephalography (EEG); electromyography (EMG); electonystagmography (ENG); electro-oculography (EOG), printed circuit electrodes, and electroretinography (ERG).

Figure 3:
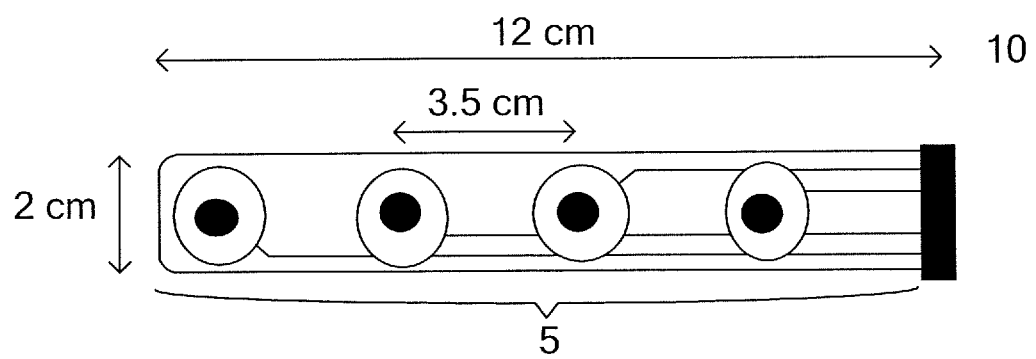
FIG. 3 illustrates a strip of electrodes or sensors that can be used in combination with the interface cable of the invention.
Figure 25:
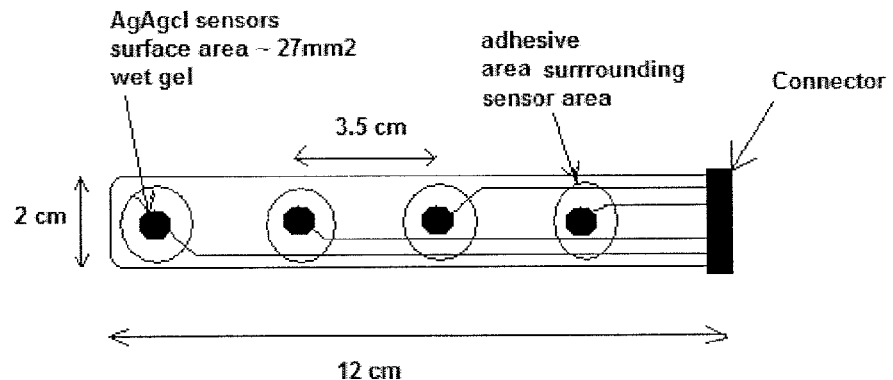
FIG. 25 illustrates a strip of electrodes or sensors that can be used in combination with the interface cable of the invention.

In a preferred embodiment, as illustrated in FIGS. 3 and 25, the interface system comprises an electrode interface for a plurality of electrodes, more preferably between 2 and 6 electrodes. Preferably, the electrodes are provided on a strip or mesh 5, including a single connector 10 for the electrode interface of the invention. The electrodes can be bipolar or monopolar in nature. The electrodes are preferably AgAgCl sensors with a surface area of 27 $mm^2$ wet gel. In certain related embodiments, there is an adhesive area surrounding the sensor area. The electrodes can be placed in a wide variety of locations on the patient, including over the uterus.

In a related embodiment, the cable uses the same power as that supplied by the maternal-fetal monitor, and thus will not require a separate power supply. In certain embodiments, as illustrated in FIGS. 2 and 24, an additional power connector is included in the system that allows for permanent power connectivity. The power connector can be designed as a semi-permanent adapter 30 connected to the maternal-fetal monitor that allows both PROBE cables 35 and an sensor cables 40 to be plugged into it without removing the adapter from the monitor 25. In this way, the power system can be attached to the monitor once and not removed, allowing repeated swapping of the PROBE cable and the interface system of the present invention without undue hassle.

The sensor interface can be connected to any conventional sensor or set of sensors including, but not limited to, disposable sensors (including sensors that are without gel or pregelled), reusable disc electrodes (including gold, silver, stainless steel, or tin electrodes), headbands, saline-based electrodes, impedance, radio frequency (RF), and acoustic sensors. Contemplated sensors include those used for monitoring electrocardiography (ECG/EKG); electroencephalography (EEG); electromyography (EMG); electronystagmography (ENG); electro-oculography (EOG), printed circuit sensors, electrorctinography (ERG), bioimpedance sensors (RF or otherwise) and stethoscope sensors.

Figure 18:
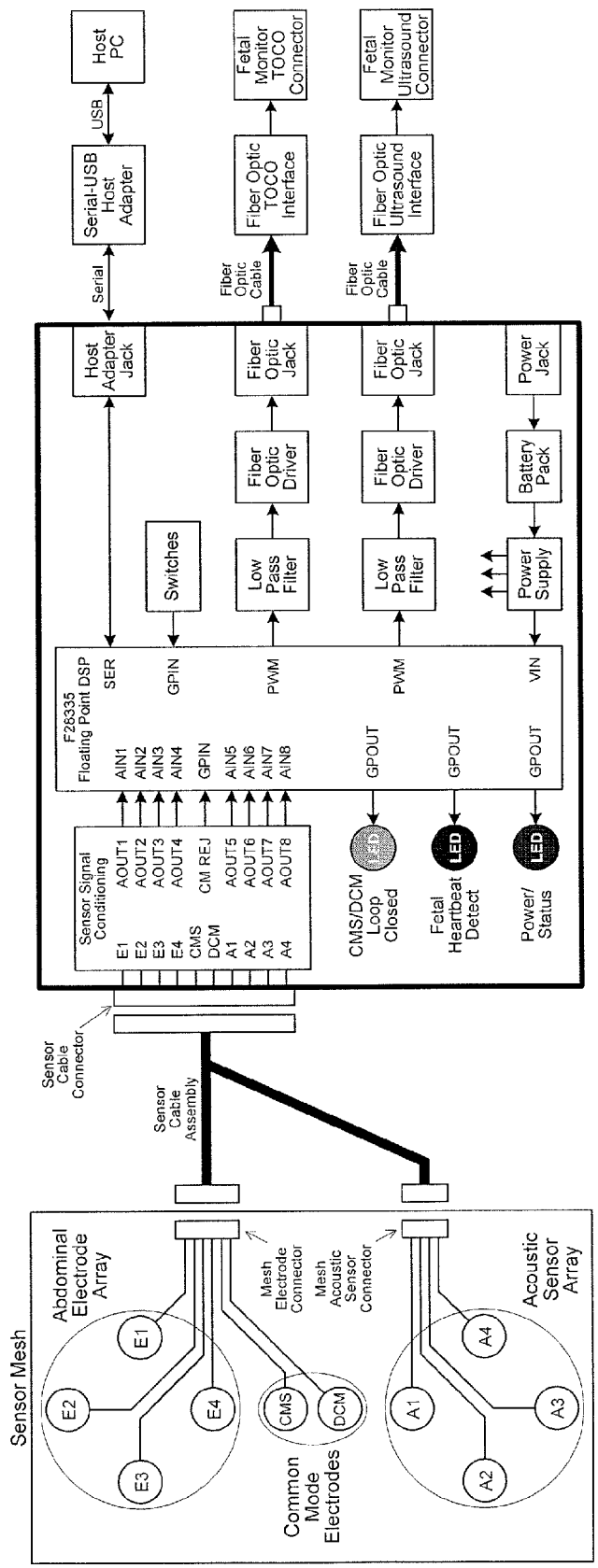
FIG. 18 illustrates a functional block diagram of a sensor interface system according to an embodiment of the subject invention. An electrode and acoustic sensor array (left) can interface to a cable containing a signal converter (middle) and a fetal monitor interface (right).

In a preferred embodiment, as illustrated in FIGS. 3 and 25, the interface system comprises a sensor interface for a plurality of sensors, more preferably between 2 and 8 sensors. FIG. 18 illustrates a functional block diagram of a sensor interlace system according to an embodiment of the subject invention. An electrode and acoustic sensor array (left) can interface to a cable containing a signal converter (middle) and a fetal monitor interface (right). Referring to FIG. 18, preferably, the sensors are provided on a strip or mesh 5, including a single connector 10 for the sensor interface of the invention. Electrode sensors can be bipolar or monopolar in nature. The electrode sensors are preferably AgAgCl sensors with a surface area of 27 mm$^2$ wet gel. In certain related embodiments, there is an adhesive area surrounding the sensor area. The sensors can be placed in a wide variety of locations on the patient, including over the uterus.

Figure 6:
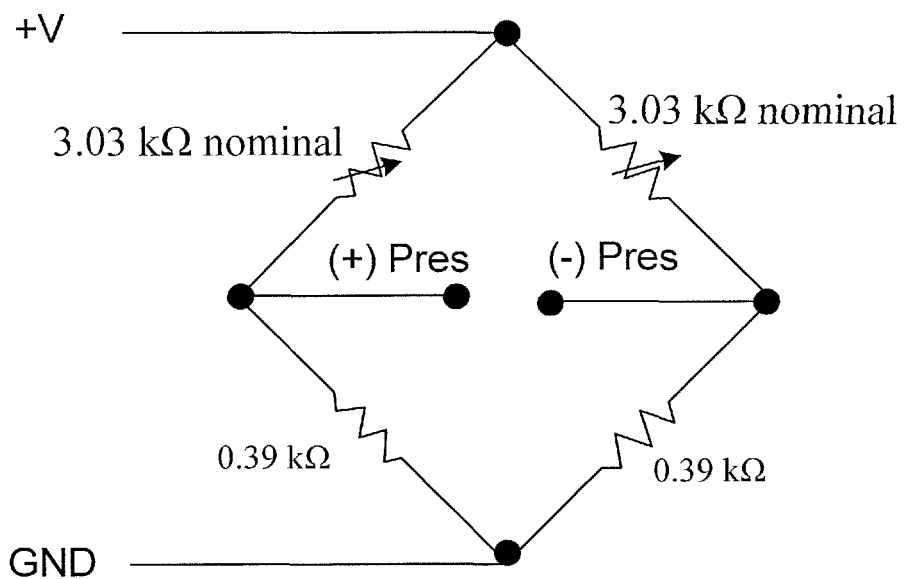
FIG. 6 illustrates one process for producing an electrical analog equivalent to a tocodynamometer signal from electrode or sensor signals.
Figure 7:
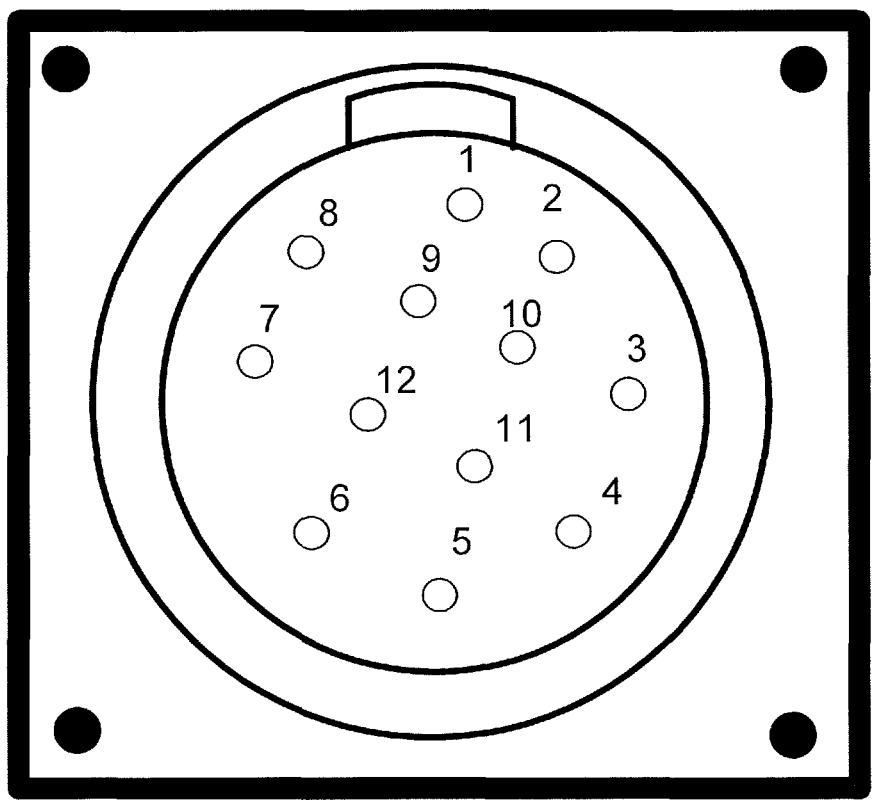
FIG. 7 illustrates a uterine activity connector pinout in a maternal-fetal monitor.
Figure 8A:
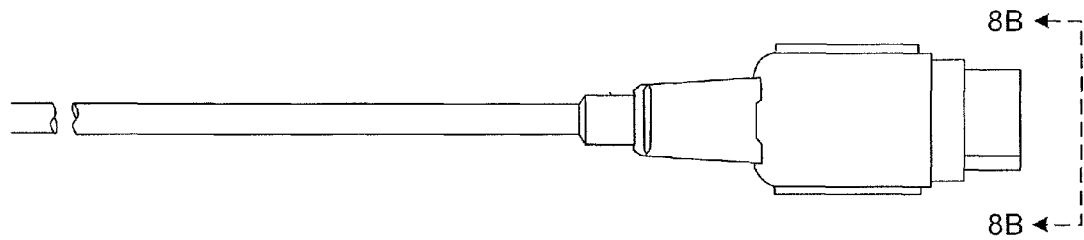
FIGS. 8A-8C illustrate a square-type cable for interfacing a fetal scalp electrode with a maternal-fetal monitor, including the cable pinout diagram and a "square-type" connector pinout for the fetal scalp electrode cable in a maternal-fetal monitor.
Figure 8B:
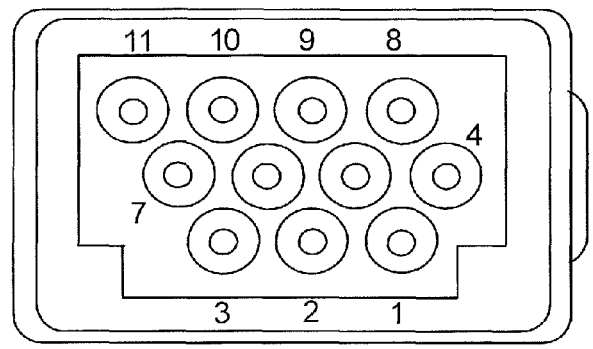
Figure 8C:
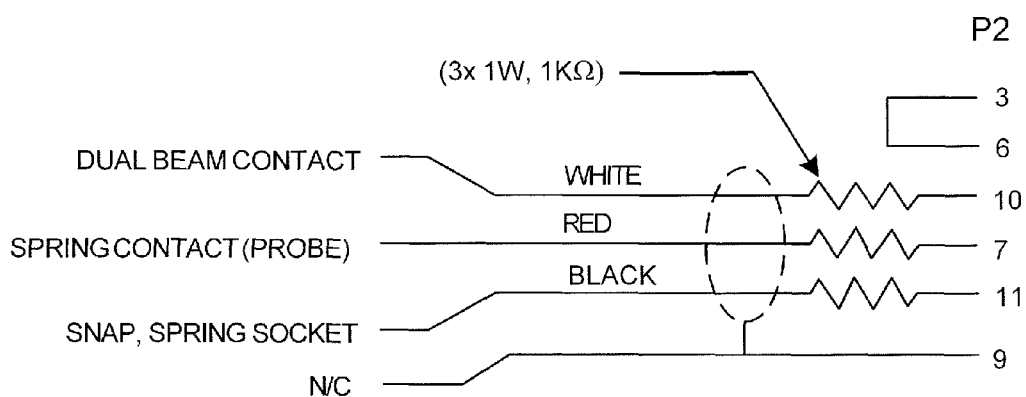
Figure 9A:
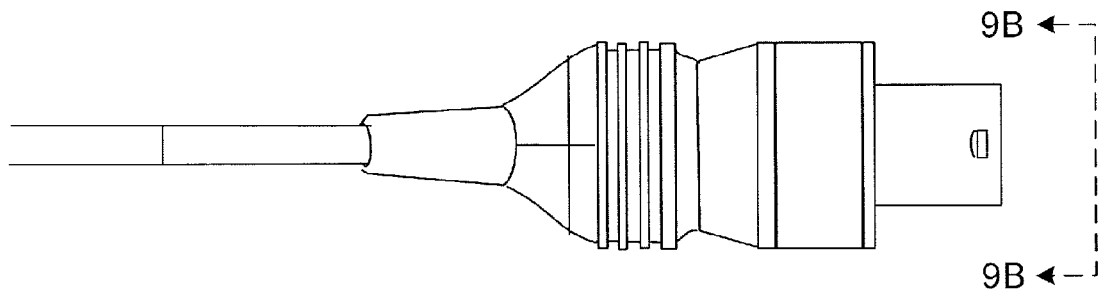
FIGS. 9A-9C illustrate another cable for interfacing a fetal scalp electrode with a maternal-fetal monitor, including the cable pinout diagram and a "circular-type" connector pinout for the fetal scalp electrode cable in a maternal-fetal monitor.
Figure 9B:
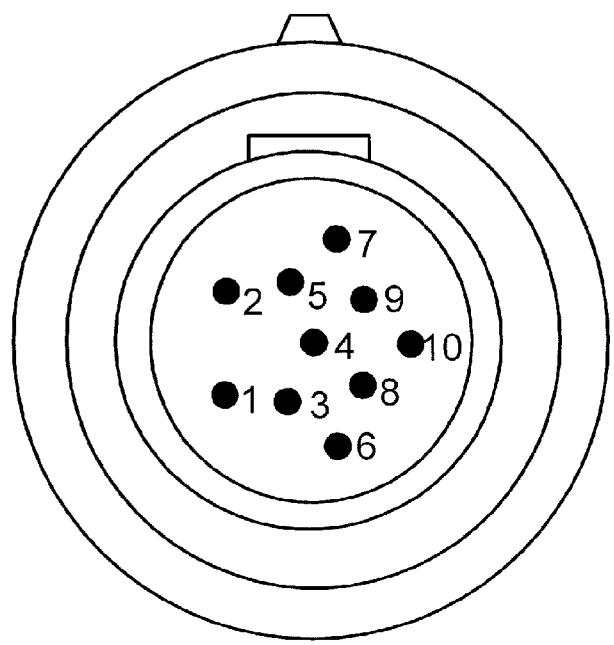
Figure 9C:
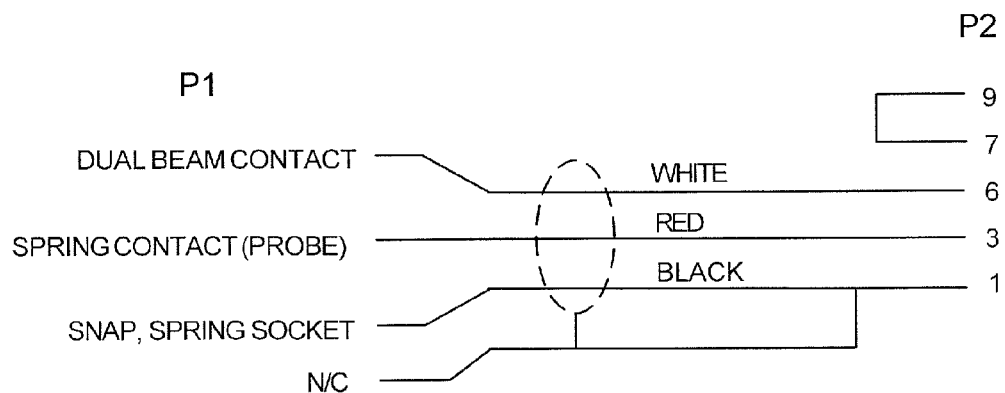
Figure 10A:
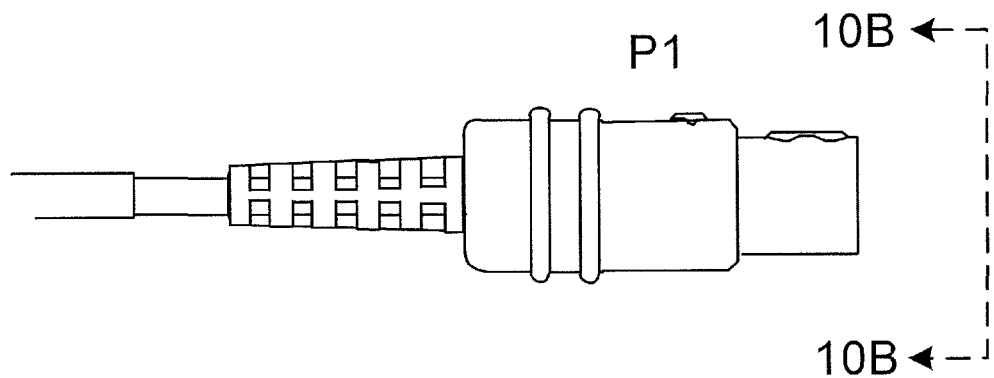
FIGS. 10A-10C illustrate a cable for interfacing an intra-uterine pressure catheter (IUPC) with a maternal-fetal monitor, including the cable pinout diagram and a "circular-type" connector pinout for the IUPC cable in a maternal-fetal monitor.
Figure 10B:
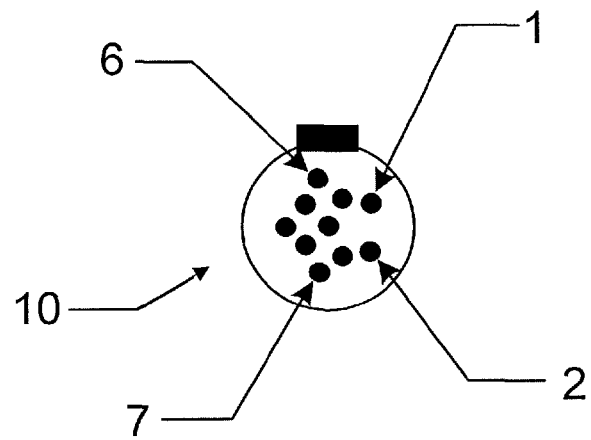
Figure 10C:
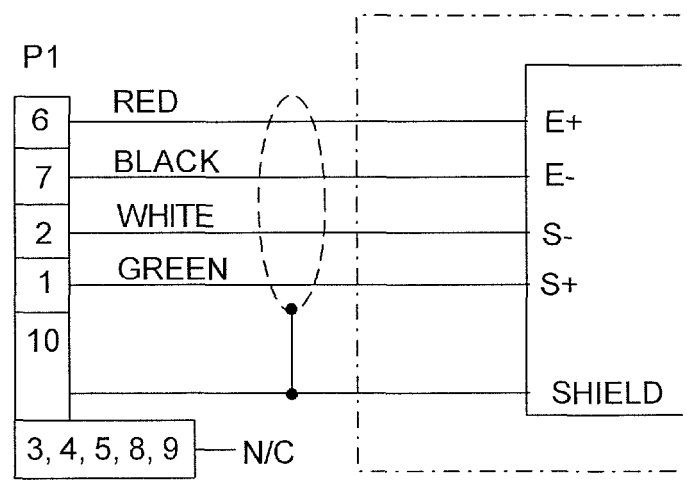
Figure 11A:
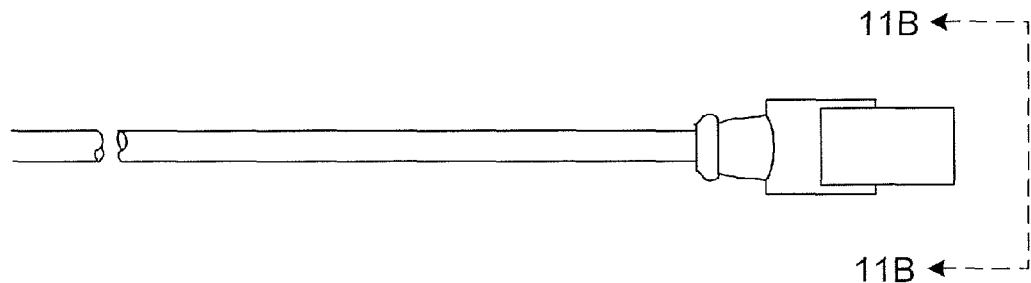
FIGS. 11A-11C illustrate yet another cable for interfacing a fetal scalp electrode with a maternal-fetal monitor, including the cable pinout diagram and the corresponding connector pinout for the fetal scalp electrode cable in a maternal-fetal monitor.
Figure 11B:
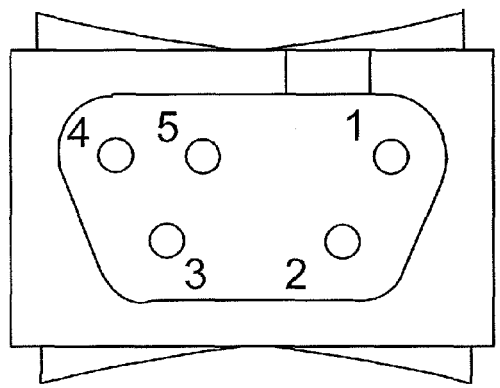
Figure 11C:
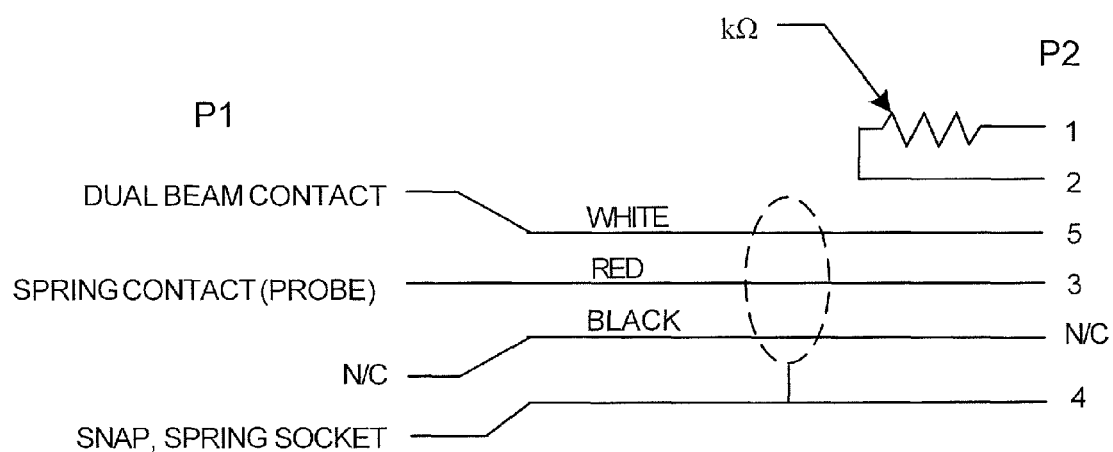
Figure 12A:
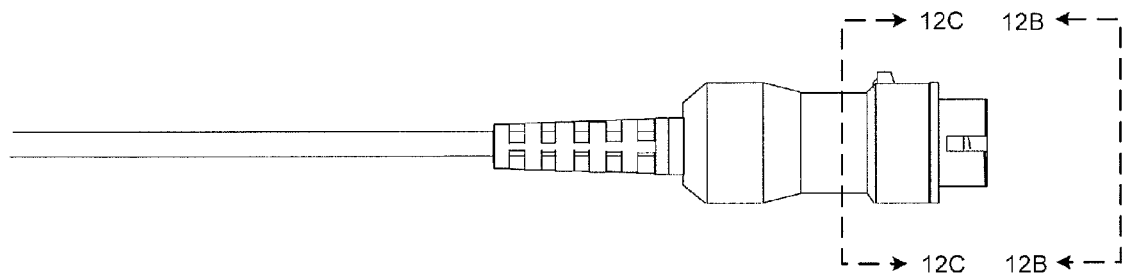
FIGS. 12A-12C illustrate another cable for interfacing an intra-uterine pressure catheter (IUPC) with a maternal-fetal monitor, including the cable pinout diagram and the corresponding connector pinout for the IUPC cable in a maternal-fetal monitor.
Figure 12B:
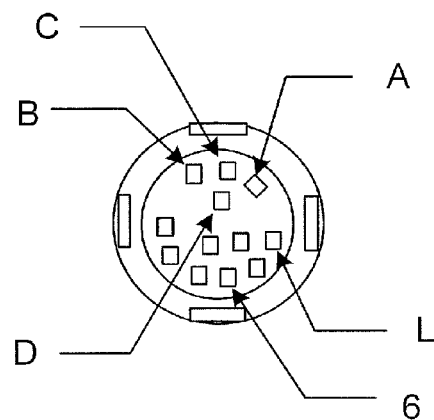
Figure 12C:
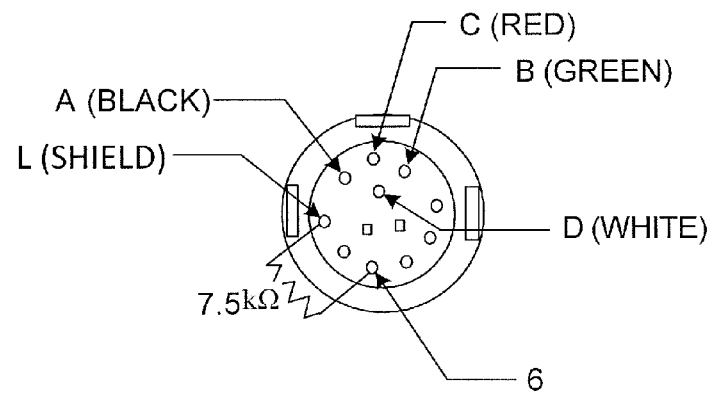
Figure 13:
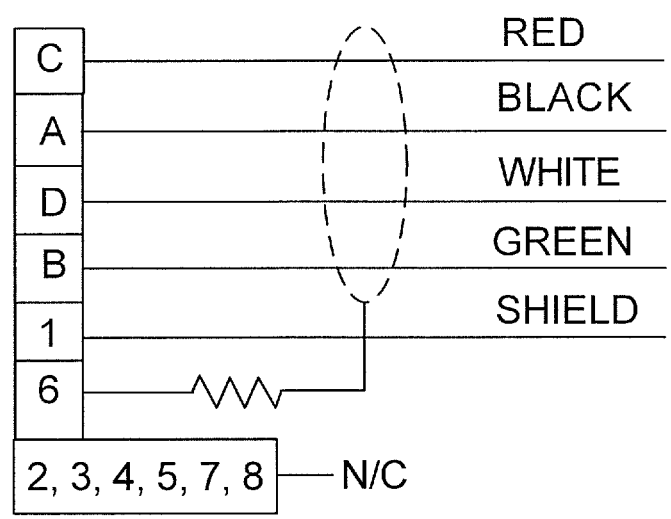
FIG. 13 illustrates identifying connection information for the cable pinout and corresponding connector pinout of FIGS. 12B and 12C.

In a preferred embodiment, the signal converter of the invention includes a microprocessor, digital signal processor, or other programmable device that converts electrode or sensor signal data into an electrical analog of a Wheatstone bridge configuration that is normally used in a tocodynamometer. An illustration of a Wheatstone bridge configuration used in a conventional tocodynamometer is illustrated in FIG. 6. A tocodynamometer generally transforms strain to the strain gauge/sensor into a proportional change of resistance. Given the linear Wheatstone bridge configuration, differential output voltages are produced that are linearly related to the strain applied to the gauge/sensor. These differential output voltages are produced at the (+) and (−) pressure ports at mV amplitude levels. In certain instances, these small differential output voltages are subsequently amplified in the fetal/maternal monitor using a differential-input instrumentation amplifier configuration.

Figure 4:
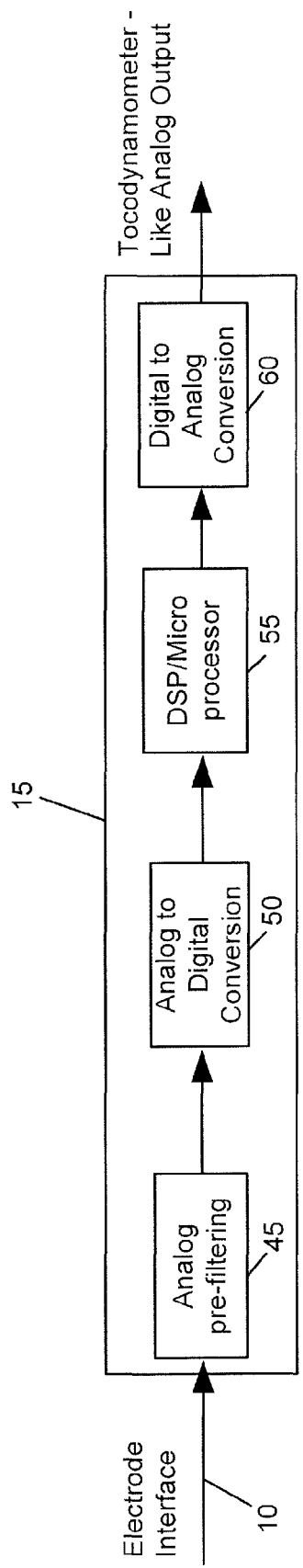
FIG. 4 is a flow diagram illustrating the process for converting electrode or sensor input to tocodynamometer-like data within the interface cable.

According to one embodiment of the subject invention, as illustrated in FIG. 4, the signal converter 15 includes a programmable device 55 and an analog to digital converter 50 that converts EHG or sensor signals derived from the electrode or sensor interface from analog signals to a digital output, where the digital output is then processed by the programmable device. The programmable device determines the appropriate voltage level required to mimic the output of the PROBE based upon the digital output signals received. This voltage level can then be converted back to an analog signal using a digital to analog converter 60, pulse width modulation circuit, or other method.

In another embodiment, the signal converter includes a microprocessor 55 that calculates the desired uterine activity from the EHG or sensor signals. The microprocessor interfaces to the monitor via a microprocessor-controlled digital potentiometer, where the potentiometer simulates the strain gauge resistances seen at the legs of the Wheatstone bridge. This solution would mimic the tocodynamometer itself, instead of just the voltages output from the tocodynamometer. The desired signal would be driven on the Wheatstone bridge in a matter similar to the tocodynamometer itself, thus creating an EHG emulation of a tocodynamometer that is more compatible with different types of fetal monitors.

Figure 19:
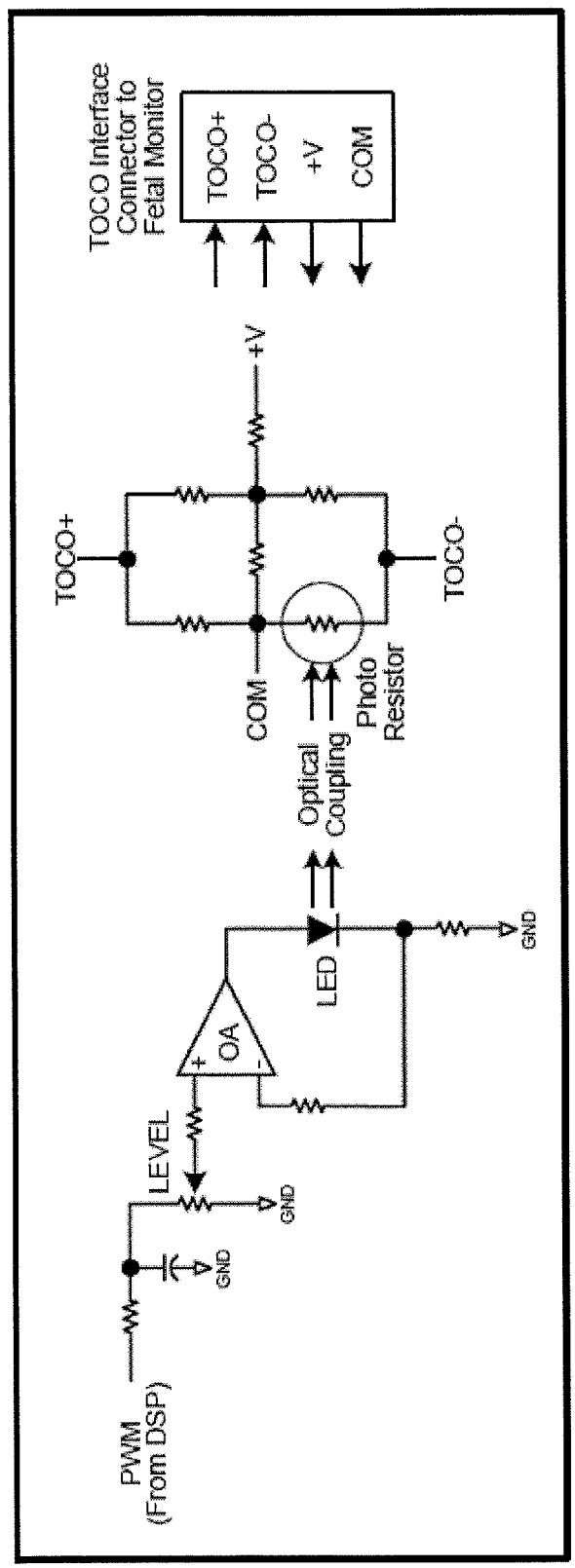
FIG. 19 illustrates a functional block diagram of a novel design, according to an embodiment of the subject invention, to interface to a toco port of an existing maternal-fetal monitor.

In a preferred embodiment, the fetal monitoring ports are driven with an optical coupling method that provides simple and effective complete electrical isolation between the system and the fetal monitor. FIG. 19 shows an interface, according to an embodiment of the subject invention, to a fetal monitor connection, e.g. a toco connection. The optical interface for the fetal monitor toco input creates an optically-isolated balanced bridge circuit that is essentially identical to a standard tocodynamometer bridge circuit, but uses a photo-resistor instead of a resistive strain gauge in one leg of the bridge. The photo-resistor is optically coupled to an LED circuit driven by a pulse-width modulated (PWM) digital-to-analog converter (ADC) and voltage-to-current converter amplifier device. The analog contraction curve signal from the ADC circuit modulates the current through the LED, and through the optical coupling to the bridge photo-resistor, creates a toco signal at the bridge outputs that is fed to the fetal monitor toco input connector.

Figure 20:
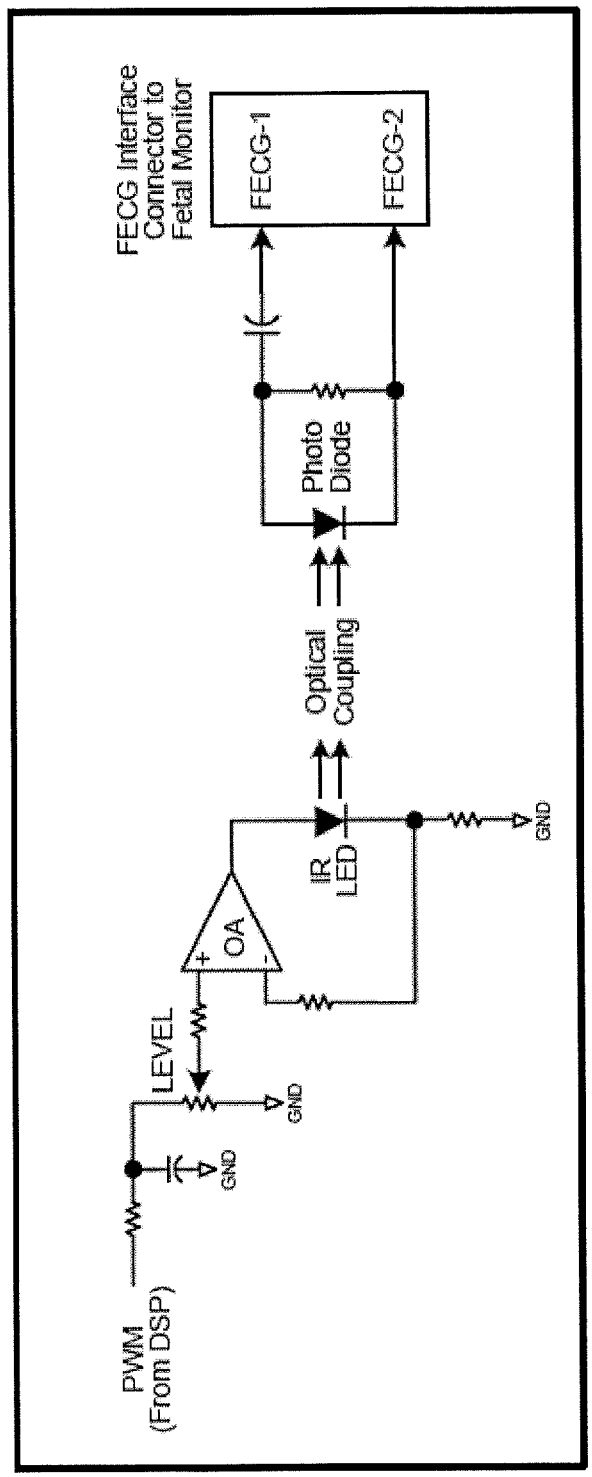
FIG. 20 illustrates a functional block diagram of a novel design, according to an embodiment of the subject invention, to interface to an FECG port of an existing maternal-fetal monitor.

FIG. 20 illustrates an optical interface, according to an embodiment of the subject invention, for the fetal monitor Fetal ECG input. It creates a millivolt-level pulse signal that simulates a fetal heartbeat ECG signal. A simulated fetal heartbeat pulse is generated by the signal converter, and it is output through the analog-to-digital converter (ADC) circuit that drives the input of a current-to-voltage amplifier circuit. The current-to-voltage amplifier drives an output current through an infrared LED that generates an optical fetal heartbeat pulse signal. This optical fetal heartbeat signal is optically coupled to a photodiode, which converts the optical signal into an electrical signal that is fed to the fetal monitor FECG input connector.

In certain embodiments, the microprocessor includes a means for filtering 45 of the signals generated from the electrodes or sensors. In one embodiment, the microprocessor includes: (1) a high pass filter at very low frequency (0.005 Hz) to remove the DC offset and noise, and (2) a low pass filtered with another low frequency filter (0.025 Hz). In a related embodiment, the microprocessor includes a high pass filter at a very low frequency and a standard power estimation method such as RMS or other squaring methods. More complex signal processing methods such as wavelets, blind source separation, nonlinear filtering, and frequency analysis can also be utilized.

Multiple signal channels can be included at the electrode or sensor interface to reduce noise characteristics. The multiple channels can be processed by the signal converter in many ways. For example, the signals can simply be added to each other or subtracted from each other for more robustness to noise. Additionally, attributes can be calculated on each signal and those signals with the best characteristics (e.g. signal to noise ratio) can be used to create the uterine activity signal.

In an alternative embodiment, the microprocessor and digital portion of the system would be replaced with a completely analog system. Analog filters can be created with resistors, capacitors, and amplifiers can be embedded into the signal converter to convert the EHG or sensor signals to PROBE-like signals. Analog circuitry can be designed using discrete components or integrated components such as ASICs (application specific integrated circuits). Since the conversion from EHG or sensor electrical interface to PROBE electrical interface is externally, simply a voltage conversion, analog filtering can be created to modify the EHG or sensor signals and create signals that mimic those expected by the fetal monitor.

In yet another embodiment, the signal converter includes both analog and digital processing. The analog processing would typically include pre- or post-processing of the signals. For example anti-aliasing filters or other filtering techniques can be implemented by the signal converter. Similarly, the signal converter could apply signal conditioning to the output signal to appropriately mimic the signal output from a PROBE.

Figure 21:
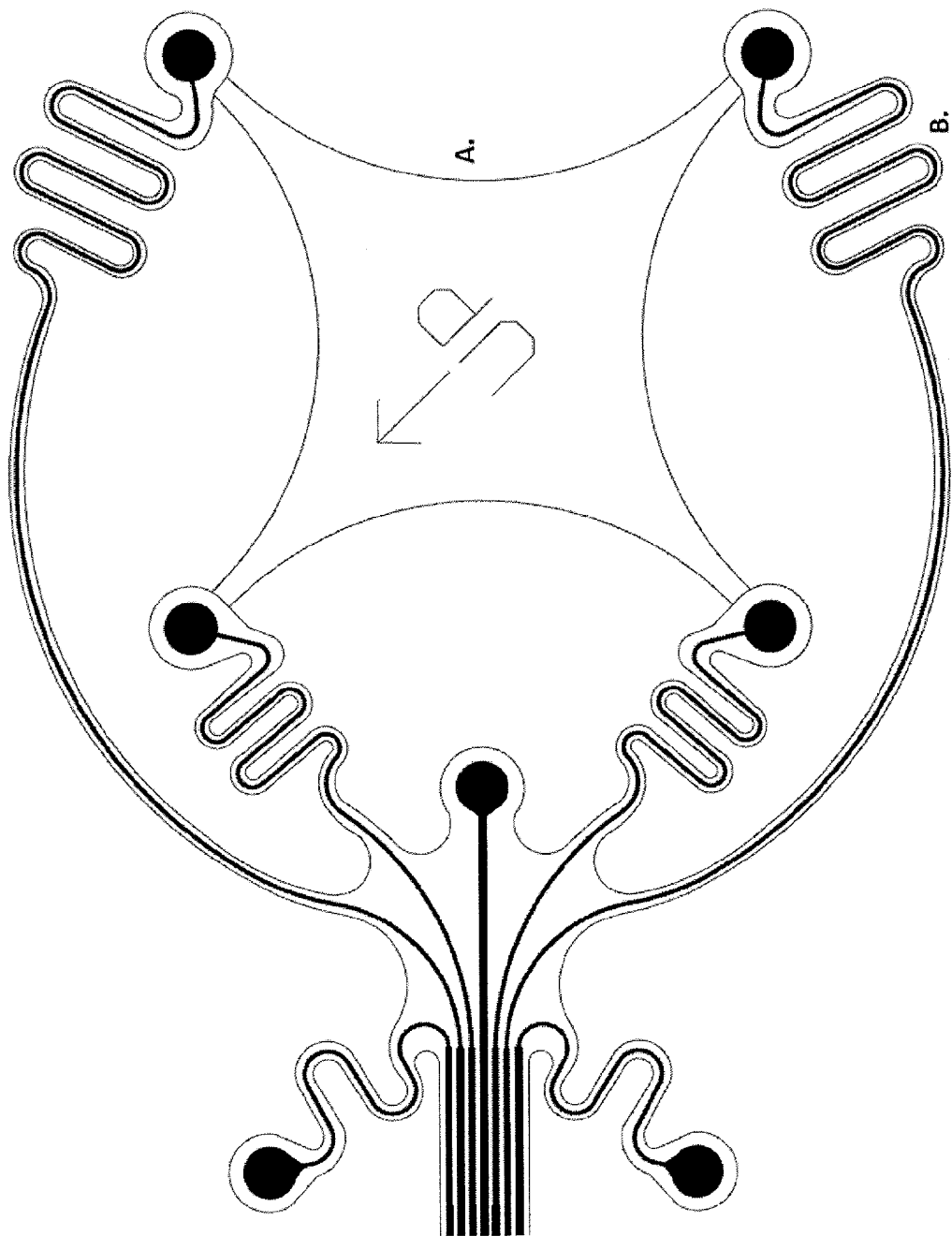
FIG. 21 illustrates a diagram of a sensor array, according to an embodiment of the subject invention, with features specifically designed for maternal abdomens.

FIG. 21 illustrates a multi-sensor interface, according to an embodiment of the subject invention, to the signal converter that is specially designed to interface to a pregnant subject's abdomen. The multi-sensor interface, herein called a mesh, is made of a substrate that contains electrical material between the connector and the sensors. The electrical material can be, for example, printed, painted, or sewn between the connector and the sensors. The curved lines in the mesh are designed to wrap around the curved surface of the maternal abdomen. The serpentine shape (B) on each arm allows the mesh to flex and stretch around different shaped abdomens and as the subject moves. The serpentine shape can be rounded or linear. Each serpentine shape can include two or more curves or changes of direction of 180 degrees or about 180 degrees. For example, each serpentine shape can include two, three, four, five, six, or more curves or changes of direction (of 180 degrees or about 180 degrees). The alignment piece (A) of the mesh, called the electrode directional alignment template (EDAT), allows for proper alignment of the mesh as well as greatly simplifying the placement of the sensor mesh. The EDAT is connected to some or all of the electrodes. The EDAT is preferably connected to some or all of the electrodes with a perforated form or tabbed release liner. The mesh comes formed with an adhesive backing and a release liner. When placed, the nurse can remove the release liner and place the sensor mesh with alignment center piece (EDAT) on the abdomen. Once placed, the alignment piece can be removed to allow the mesh to move freely and comfortably on the maternal abdomen while maintaining good connectivity.

Figure 22:
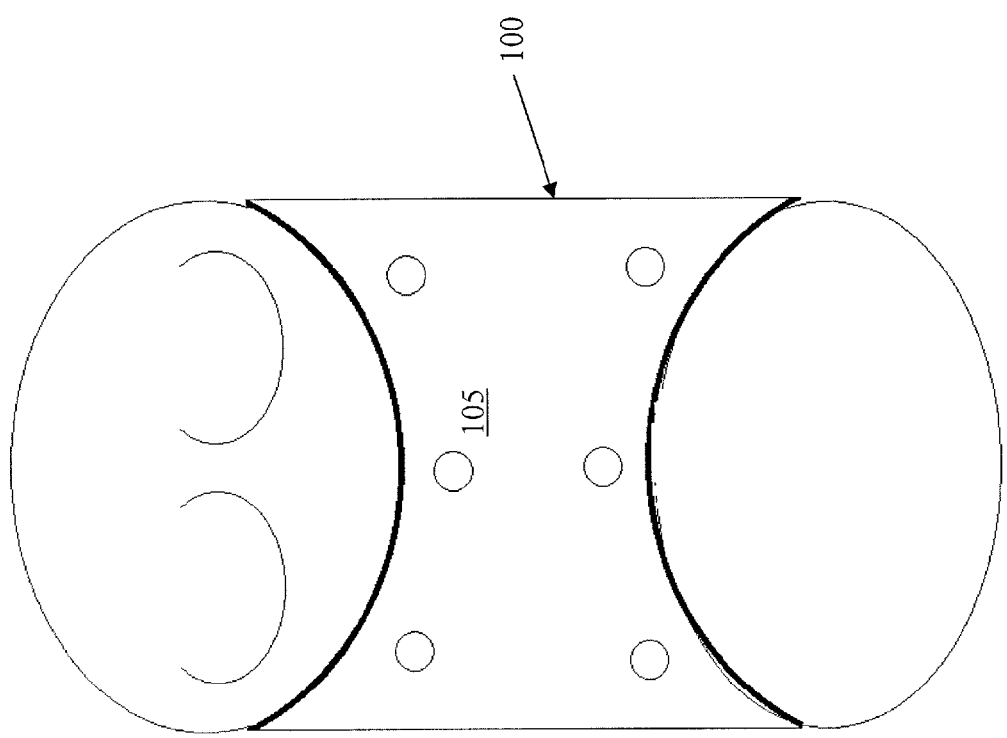
FIG. 22 illustrates a sensor array template, according to an embodiment of the subject invention, for utilizing off the shelf sensors.

FIG. 22 illustrates a template, according to an embodiment of the subject invention, that allows individual sensors to be connected to the system with accurate placement and cable management. The template 105 can be made of, for example, fabric or plastic. The template 105 has mechanisms to hold the sensors in place at different locations on the abdomen 100 while including mechanisms to hold the wires between the sensors and connector in place. The wires can be, for example, painted, printed, or sewn onto/into the substrate.

In another embodiment, acoustic sensors are included. The heart's periodic activity is controlled by an electrical conducting system. This system initiates the electrical signal in specialized pacemaker cells that are then propagated through the atria to the AV-node and to the ventricles. In turn, this electrical action potential (used in ECG analysis) excites the muscle cells and causes the mechanical contraction of the heart chambers from which four audible heart sounds are generated. The sequence of events that generates the heart sounds is often referred to as the cardiac cycle.

Figure 16:
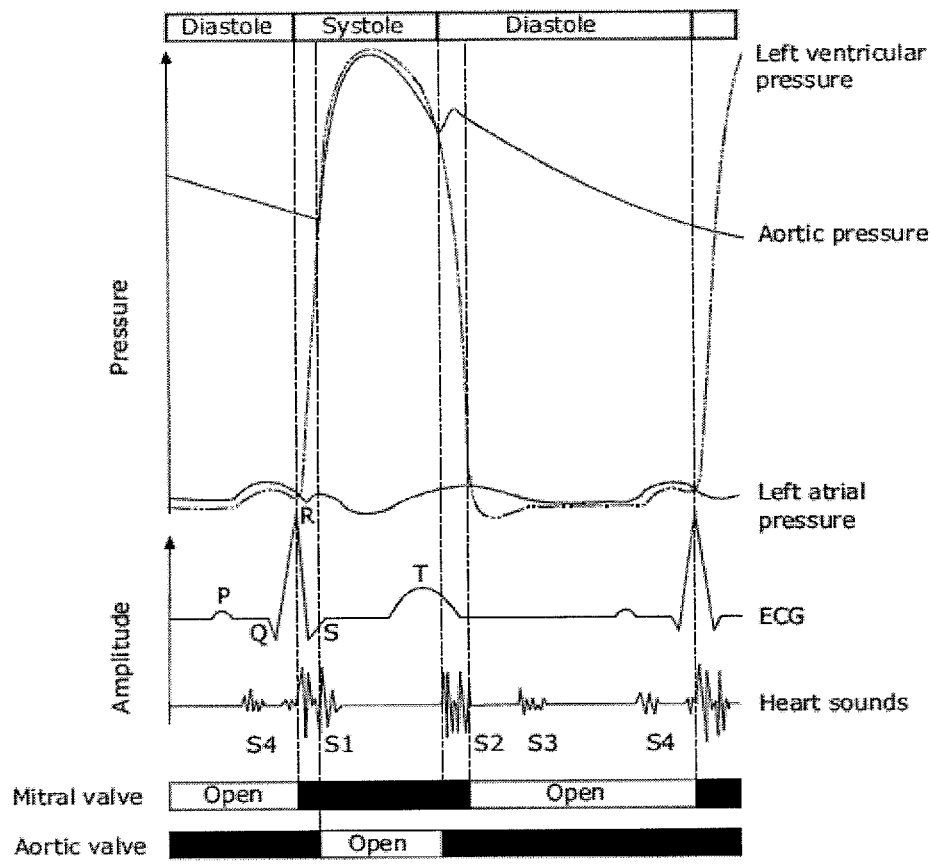
FIG. 16 illustrates heart sounds in relation to hemodynamic events and ECGs.

FIG. 16 illustrates how the four heart sounds are correlated to the electrical and mechanical events of the cardiac cycle. The first heart sound (S1) occurs during the systole phase of the cardiac cycle. It is characterized by a higher amplitude and longer duration in comparison with other heart sounds. The duration of S1 lasts for an average period of 100-200 ms. It also has two major high-frequency components in the range of 10-200 Hz that can be easily distinguished. These two components are often separated by a time delay of 20-30 ms and coincide with the RS interval of the electrocardiogram (ECG). Overall, the acoustic properties of S1 are able to reveal the strength of the myocardial systole and the status of the atrioventricular valves' function.

The second heart sound (S2) occurs during the diastole phase and coincides with the completion of the T-wave of the ECG. The produced sound usually has higher-frequency components (as high as 400 Hz) as compared with the first heart sound. Since the aortic valve tends to close before the pulmonary valve, the interval between the components can often vary. Further variations of the time interval can be caused by respiration. For example, during expiration phase, the interval between the two components is small (less than 30 ms). However, during inspiration, the interval between the two components is much larger.

The third (S3) and fourth heart sounds (S4), also called gallop sounds, are low-frequency sounds (15-60 Hz) occurring in early and late diastole (within 120 ms P-wave of the ECG), respectively. Although a normal S3 is audible in children and adolescents it is not audible in most adults. Alternatively, the fourth heart sound is seldom audible in normal individuals without the use of highly sensitive sensors.

Overall, the different heart sounds give us various pieces of information about the cardiac activity. Integrating this information with the information provided by the electrical conducting system (through the use of ECG) should yield better signal processing techniques or improvements on existing methods.

Using the acoustic information allows easier acquisition of the Fetal Heart Rate (FHR). Under normal conditions, the Fetal Electrocardiogram (FECG) is susceptible to noise interference of the mother's electrical signal and/or muscle contractions. Using the acoustic information of the mother and child help refine the independent signals and provide for more robust separations since the acoustic information would not be effected by the mother's contractions. Additionally, S3 and S4 are only observable in the healthy hearts of children. This may allow for another way to separate the maternal heart rate from the fetus.

Figure 17:
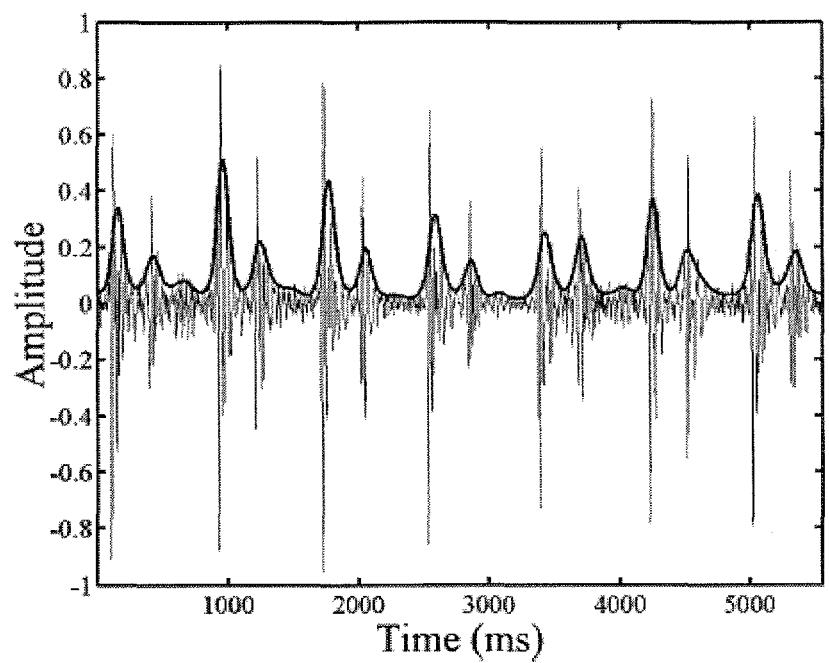
FIG. 17 illustrates an enveloped signal.

One algorithm for acquiring the FHR involves detecting the maternal heart rate (MHR) in the ECG signal. This would include channel averaging or subtraction across the four ECG channels to remove noise. Then a detection of the periodic signal with the most energy should correspond to the heart rate of the mother. Once the MHR signal is acquired, a matched filter could be formed from a portion of the QRS MHR signal and summarily subtracted from the filtered version of the MHR. This process should leave most of the FHR on the ECG signal and attenuate the MHR. Finally, a low-passed average energy measure would be applied to the remaining signal in order to generate a signal envelope (FIG. 17). This would complete phase one.

Phase two would require a similar process on the phonocardiogram. Although there may be a dependence on the location of the acoustic sensors, the channels can first be averaged or subtracted to eliminate noise. Then homomorphic filtering would be applied to the cleaned phonocardiogram along with a low passed-average energy measure in order to generate a signal envelope. As above, the periodic signal can be detected with the largest energy to determine the maternal heart signal. The matched filtered version of the enveloped signal can then be subtracted from the enveloped signal. This would leave S2 and the fetal phonocardiogram signals. Another pass of the above described algorithm would be used to remove S2 and leave the fetal acoustic signal.

For the final phase of the algorithm, the FHR signal envelope acquired from the ECG would be cross correlated with the FHR signal envelope acquired from phonocardiogram at different lags (under 200 ms). The correlation peaks would relate to a true FHR signal (using some sort of peak detector).

Figure 5:
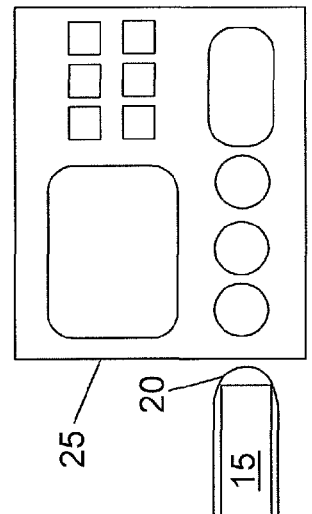
FIG. 5 illustrates another embodiment of the invention comprising a wireless interface connection between an electrode strip or sensor strip and maternal-fetal monitor.
Figure 5:
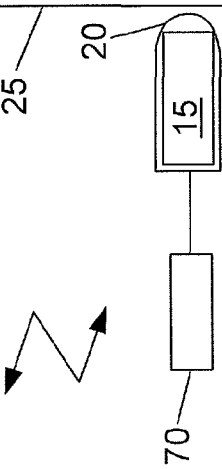
Figure 5:
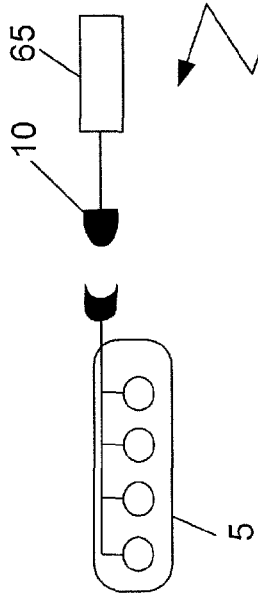
Figure 26:
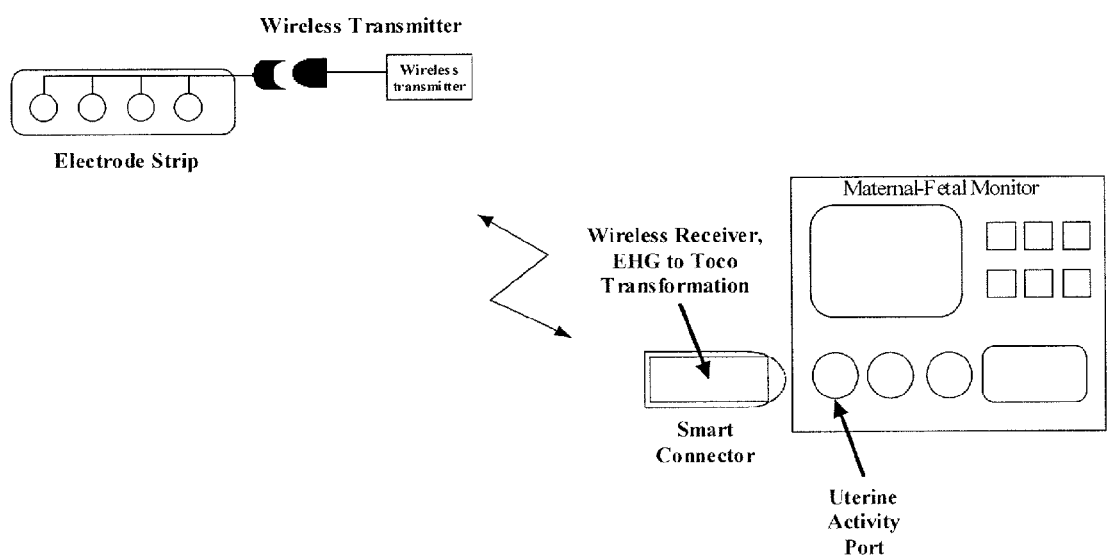
FIG. 26 illustrates another embodiment of the invention comprising a wireless interface connection between an electrode strip or sensor strip and maternal-fetal monitor.

A wireless embodiment is contemplated herein, see FIGS. 5 and 26. The interface system comprises an electrode or sensor interface 10, a wireless signal transmitter 65, a wireless signal receiver 70, a signal converter 15, and a maternal-fetal monitor port interface 20. According to the subject invention, these components can be physically independent from each other or presented in various combinations to form a single component. For example, the electrode or sensor interface and wireless signal transmitter can be presented together as a single component; the wireless signal receiver and signal converter can be presented together as a single component; the signal converter and wireless signal transmitter can be presented together as a single component; the maternal-fetal port interface, the signal converter, and the wireless signal receiver can be presented together as a single component.

According to one embodiment, a wireless signal transmitter is operably connected to an electrode or sensor interface, which is connected to the electrode(s) or sensor(s). The wireless signal transmitter can include a data storage device (such as a magnetic hard drive, flash memory card, and the like).

Preferably, the wireless signal transmitter includes communications protocols for data representation, signaling, authentication, and error detection that is required to send information over a wireless communications channel (i.e., a specific radio frequency or band of frequencies such as Wi-Fi, which consists of unlicensed channels 1-13 from 2412 MHz to 2484 MHz in 5 MHz steps). The wireless signal transmitter is preferably located in close proximity to the patient or on the patient's body. For example, the wireless signal transmitter can be attached to the side of the bed or the patient's arm. In certain embodiments, the signal converter is operably connected to the wireless signal transmitter or presented together with the wireless signal transmitter as a single component.

A wireless signal receiver is also included in the wireless embodiment. The wireless signal receiver is operably connected to a signal converter and/or maternal-fetal monitor port interface. The wireless signal receiver is preferably configured with communications protocols to receive information over a wireless communications channel.

Many wireless transmission communications protocols exist and are applicable to the wireless signal transmitter/receiver of this invention, including Bluetooth, Wi-Fi, Zigbie, wireless USB, etc. The wireless transmission of information from the wireless signal transmitter to the wireless signal receiver could be in digital format or in analog format.

In certain embodiments, the wireless signal transmitter (and/or wireless signal receiver) includes an internal power source (i.e., batteries, and the like). Alternatively, the wireless signal transmitter (and/or wireless signal receiver) does not require an internal power source. This can be accomplished with a variety of energy harvesting or wireless power transmission methods such as harvesting of heat, movement, electrical signals from the environment, or inductive coupling. In one embodiment, this is accomplished by using an antenna to convert radiated or inducted power into usable energy for the transmission of the desired signals. For example, the wireless signal transmitter can be an antenna that is commonly used in radio frequency identification tags (or RFID tags), where minute electrical current induced in the antenna by an incoming radio frequency signal provides just enough power for an integrated circuit (IC) in the RFID tag to power up and transmit a response (for example, to a wireless signal receiver of the invention).

In another embodiment, the EHG or sensor signal is digitized and stored in memory either in the electrode or sensor interface, the signal converter, or the maternal-fetal monitor port interface. The stored data can be transmitted periodically or at a later time. This delayed transmission may, without restriction, be utilized to improve battery life by transmitting data transiently, instead of continuously; or to allow for patient monitoring during disconnection from the monitor.

In operation, the electrode or sensor interface accepts EHG or sensor signals from the electrode(s) or sensor(s) and transmits the signals to the maternal-fetal port interface via the wireless signal transmitter and wireless signal receiver. The signal converter can be operably connected to either the wireless signal transmitter or the wireless signal receiver, where the signal converter processes the electrode or sensor signals and/or performs digital/analog signal conversions.

In one embodiment, the electrode interface attached to the electrodes contains a signal converter that can perform analog to digital conversion and process EHG signals into an equivalent tocodynamometer or IUPC voltage. The wireless signal transmitter would then digitally transmit this data to the wireless signal receiver, which would communicate the data through the maternal-fetal port interface to the maternal-fetal monitor. Preferably, the data provided to the maternal-fetal monitor mimics data format normally provided by a tocodynamometer or IUPC.

In one embodiment, the sensor interface attached to the sensors contains a signal converter that can perform analog to digital conversion and process signals into an equivalent PROBE. The wireless signal transmitter would then digitally transmit this data to the wireless signal receiver, which would communicate the data through the maternal-fetal port interface to the maternal-fetal monitor. Preferably, the data provided to the maternal-fetal monitor mimics data format normally provided by a PROBE.

In another embodiment, the electrode interface includes a means for converting analog signals to digital signals, and the resultant digital signals are transmitted via the wireless signal transmitter to the wireless signal receiver. The wireless signal receiver is operably connected to a signal converter that processes the digital signals into a format equivalent to tocodynamometer or IUPC data, which is subsequently communicated to the maternal-fetal monitor via the maternal-fetal monitor port interface.

In another embodiment, the sensor interface includes a means for converting analog signals to digital signals, and the resultant digital signals are transmitted via the wireless signal transmitter to the wireless signal receiver. The wireless signal receiver is operably connected to a signal converter that processes the digital signals into a format equivalent to PROBE data, which is subsequently communicated to the maternal-fetal monitor via the maternal-fetal monitor port interface.

In yet another embodiment, the raw analog signals generated by the electrodes are communicated via the electrode interface and wireless signal transmitter to a wireless signal receiver. The wireless signal receiver is operably connected to a signal converter that converts the raw analog signals to digital signals, which are subsequently processed by the signal converter into a format equivalent to tocodynamometer or IUPC data. The tocodynamometer or IUPC data is subsequently communicated to the maternal-fetal monitor via the maternal-fetal monitor port interface.

In yet another embodiment, the raw analog signals generated by the sensors are communicated via the sensor interface and wireless signal transmitter to a wireless signal receiver. The wireless signal receiver is operably connected to a signal converter that converts the raw analog signals to digital signals, which are subsequently processed by the signal converter into a format equivalent to PROBE data. The PROBE data is subsequently communicated to the maternal-fetal monitor via the maternal-fetal monitor port interface.

According to the present invention, the electrode or sensor interface can also be operably connected to a fetal heart rate sensor (such as an ultrasound, fetal scalp electrode, or fetal scalp sensor) with or without a uterine activity sensor. Data collected from the fetal heart rate sensor can be communicated to a maternal-fetal monitor via the cable embodiment or the wireless embodiment described above.

Figure 15:
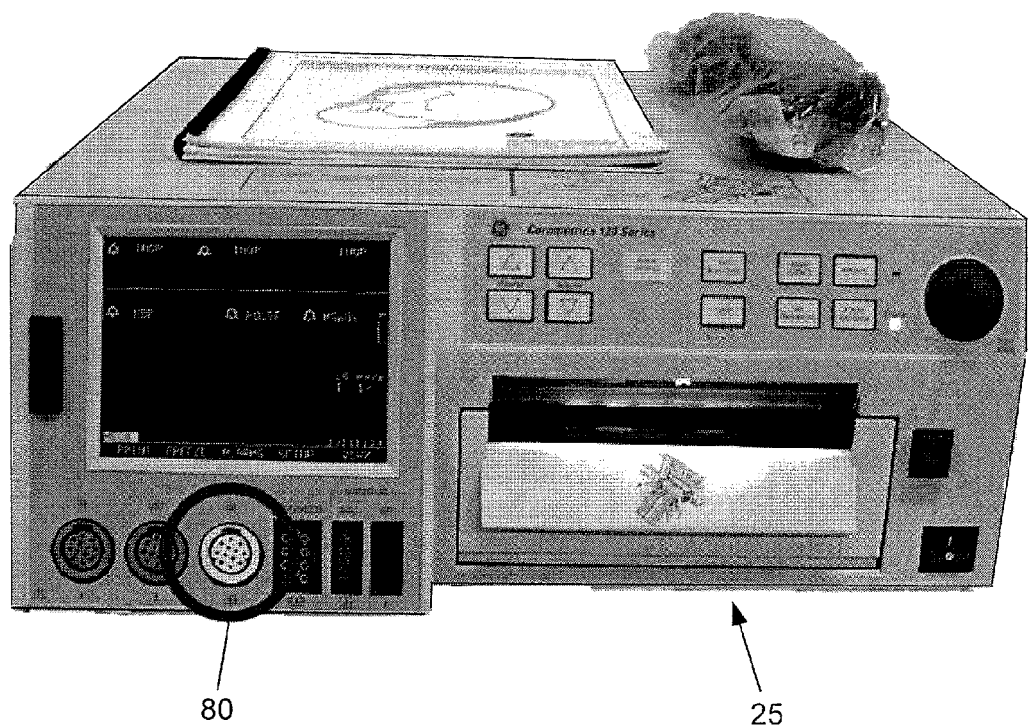
FIG. 15 illustrates a maternal-fetal monitor including a connector pinout suitable for use with the interface cable of the invention.

As illustrated in FIG. 15, the maternal-fetal monitor port interface of the invention can be operatively connected to a maternal-fetal monitor port 80 (also referred to herein as a pinout) configured for a conventional uterine activity sensor (such as a tocodynamometer, an intrauterine pressure catheter, a fetal scalp electrode, fetal scalp sensor, and the like). Preferably, the maternal-fetal monitor port interface is operably connectable with a uterine activity port or a tocodynamometer port available on a conventional maternal-fetal monitor 25. Similarly, the system interfaces to a FECG or U/S port to provide fetal cardiac data.

Maternal-fetal monitor port interface preferably consists of appropriate connectors to maternal-fetal monitors from different manufacturers having different pinout/port configurations (see FIGS. 7-13). One such example of interfacing to both COROMETRICS® and AGILENT® is provided by the METRON® PS-320 patient simulator. This simulator uses a number of custom cables for interface to these monitors. Pinout/port information for commonly available maternal-fetal monitors are provided in Table 1:

TABLE 1

Uterine Activity Connector Pinout for Corometrics 116 Monitor

| Pin # | Signal Name | Signal Description |
|---|---|---|
| 1 | (+) Pressure | Positive Input to Pressure Amp |
| 2 | (−) Pressure | Negative Input to Pressure Amp |
| 3 | NC | No Connection |
| 4 | +4 Volt Excitation | +4 Volt Reference to Bridge |
| 5 | NC | No Connection |
| 6 | GND (Excitation Ref) | +4 Volt Reference Ground |
| 7 | UA Shield | Shield |
| 8 | NC | No Connection |
| 9 | NC | No Connection |
| 10 | NC | No Connection |
| 11 | IUP Enable | IUP ENABLE (ACTIVE LOW) |
| 12 | TOCO Enable | TOCO ENABLE (ACTIVE LOW) |

EXAMPLE 1

As noted above, labor contractions are typically monitored with a strain gauge (such as a tocodynamometer), which provides frequency and approximate duration of labor contractions. Unfortunately, in obese patients, the distance from the skin to the uterus may be such that the tocodynamometer does not detect contractions reliably. In this setting, or when quantitative measurement of intrauterine pressure (IUP) is deemed necessary, an invasive IUP catheter (IUP) is commonly required. The electrical activity of the uterus, or electrohysterogram (EHG) as monitored using sensors, has long been recognized as linked to mechanical activity. This Example provides a study that compared the accuracy of EHG-derived contractions with those provided by a tocodynamometer and IUP monitoring in clinically severely obese laboring women.

Participants

This Example evaluated data from 14 laboring subjects with body mass index (BMI)≥34 who had an IUPC placed during EHG monitoring. 30 minute segments were selected before and after placement.

Methods

An array of eight 3-cm$^2$ Ag/AgCl$_2$ electrodes was placed over maternal abdomen and signals amplified with high gain, low noise amplifiers. All signals were measured with respect to a reference electrode, with driven right leg circuitry to reduce common mode noise. The amplifier 3 dB bandwidth was 0.1 Hz to 100 Hz, with a 60 Hz notch. The contraction location was derived by down-sampling the signal at 20 Hz. Contractions were rejected if duration was less than 30 seconds or greater than 120 seconds, with an amplitude less than 30% of the median of the last 10 contractions (a minimum amplitude of 5 units was also applied for each tocodynamometer/IUPC). The contraction correlation index (CCI)[1]=# consistent contractions/½(# tocodynamometer/IUPC-derived contractions+# EHG-derived contractions) was evaluated. In addition, the frequency of unreliable uterine activity monitoring, using IUP as the standard for comparison, was also evaluated.

Results

Figure 14:
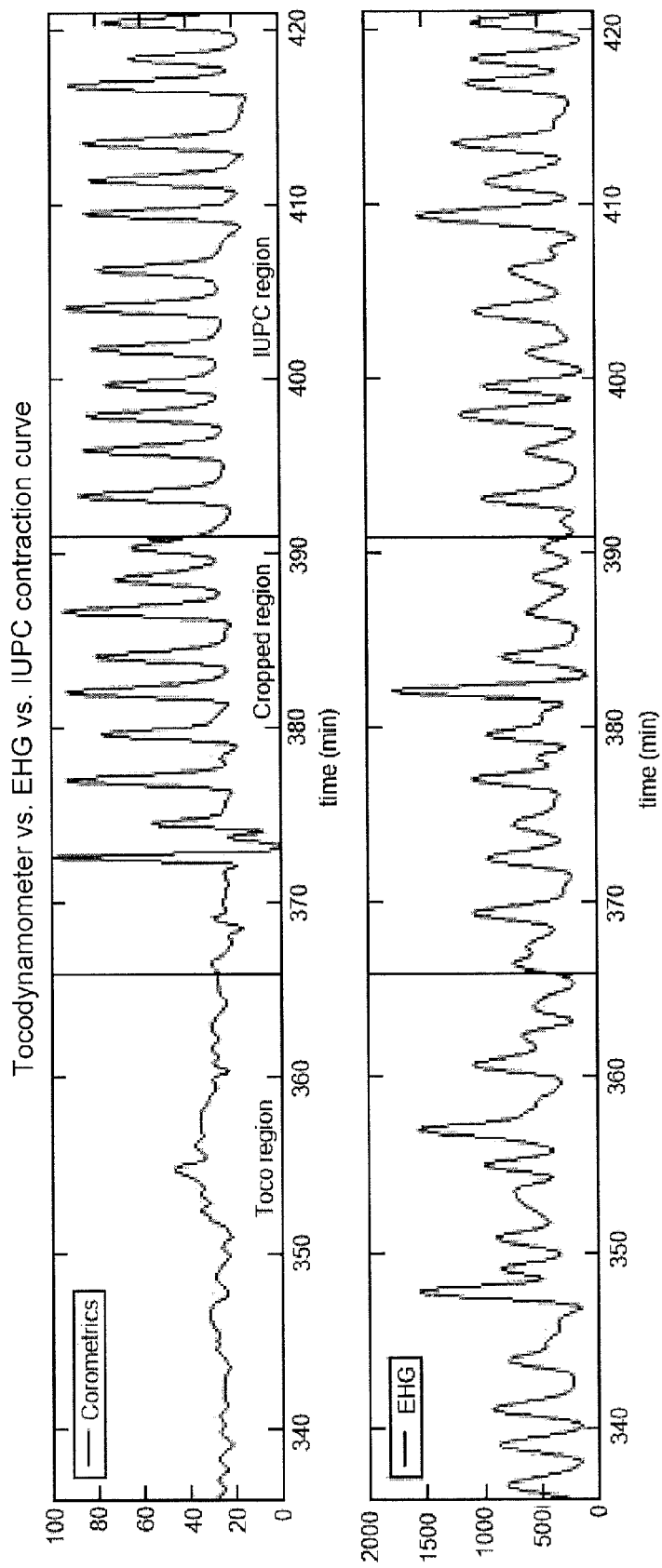
FIG. 14 illustrates the differences in accuracy for contraction patterns monitored in obese women with a tocodynamometer versus EHG-derived contraction patterns.

Of the 14 patients (BMI 45.1±7.9), 6 underwent amniotomy at the time of IUPC placement. During the first half of the study, the tocodynamometer identified 155 contractions while the EHG identified 195 contractions. After placement of the IUP, the IUP identified 192 contractions, versus 185 MG-derived contractions. The CCI between EHG and the tocodynamometer was 0.79±0.29 and the CCI was 0.92±12 between EHG and IUP (p=0.07, ns). These results demonstrate that the tocodynamometer may be unreliable in clinically severely obese patients. As illustrated in FIG. 14, the EHG-derived contraction pattern in the obese women in this study correlated better with IUP than the tocodynamometer, exceeding 90% correlation in 13/14 patients versus 10/14 for the tocodynamometer.

All patents, patent applications, provisional applications, and publications referred to or cited herein are incorporated by reference in their entirety, including all figures and tables, to the extent they are not inconsistent with the explicit teachings or this specification.

It should be understood that the examples and embodiments described herein are for illustrative purposes only and that various modifications or changes in light thereof will be suggested to persons skilled in the art and are to be included within the spirit and purview of this application.

We claim:

1. An interface system for interfacing a plurality of electrodes with a maternal-fetal monitor, wherein the maternal-fetal monitor has a port configured to operably connect with, receive output from, and display output from at least one of a tocodynamometer, an intrauterine pressure catheter, or a fetal scalp electrode, wherein the interface system comprises:
  a sensor array dimensioned to attach to a maternal abdomen, wherein the sensor array comprises the plurality of electrodes and wherein each of the plurality of electrodes is configured to detect a physiological signal;
  a first component comprising:
    an electrode interface configured to operably and removably connect with the sensor array and to receive the physiological signals from the plurality of electrodes; and
    a wireless signal transmitter configured to receive the physiological signals from the electrode interface and to wirelessly transmit the received physiological signals to a wireless signal receiver located remote from the first component; and
  a second component comprising:
    the wireless signal receiver configured to receive the physiological signals transmitted by the wireless signal transmitter;
    a signal converter configured to receive the physiological signals from the wireless signal receiver and to process the physiological signals into output data that mimics electrical output from the at least one of the tocodynamometer, the intrauterine pressure catheter, or the fetal scalp electrode; and
    a maternal-fetal monitor port interface configured to operably and removably connect to the port of the maternal-fetal monitor, wherein the maternal-fetal monitor port interface is configured to receive the output data from the signal converter and to communicate to the maternal-fetal monitor the output data when the maternal-fetal monitor port interface is connected to the port of the maternal-fetal monitor.

2. The interface system of claim 1, wherein the sensor array includes a curved arm with one of the plurality of electrodes located at a distal region of the curved arm.

3. The interface system of claim 2, wherein the sensor array includes a plurality of curved arms, each having one of the plurality of electrodes located at a distal region of the curved arm.

4. The interface system of claim 1, wherein the sensor array includes a portion having a serpentine shape that is configured to allow the sensor array to conform to a shape of the maternal abdomen.

5. The interface system of claim 4, wherein the sensor array includes a plurality of portions having a serpentine shape.

6. The interface system of claim 1, wherein the sensor array comprises between 2 and 8 electrodes.

7. The interface system of claim 1, wherein the sensor array is disposable and wherein the first component and the second component are both reusable.

8. The interface system of claim 1, wherein the sensor array is formed of a mesh.

9. The interface system of claim 1, wherein the sensor array further comprises an alignment template.

10. The interface system of claim 9, wherein the alignment template is removably coupled to the sensor array.

11. The interface system of claim 1, wherein the plurality of electrodes includes an electrode configured to detect at least one of an electrocardiography signal or an electromyography signal.

12. The interface system of claim 1, wherein the first component further comprises an analog-to-digital converter, wherein:
    the analog-to-digital converter is configured to receive the physiological signals as analog physiological signals and to convert the analog physiological signals into digital physiological signals;
    the wireless signal transmitter is further configured to wirelessly transmit the digital physiological signals;
    the wireless signal receiver s further configured to receive the digital physiological signals; and
    the signal converter is further configured to process the digital physiological signals into the output data.

13. The interface system of claim 12, wherein the signal converter is further configured to perform a digital-to-analog conversion of the digital physiological signals to generate the output.

14. The interface system of claim 1, wherein the signal converter comprises a microprocessor.

15. The interface system of claim 1, wherein the wireless signal transmitter is further configured to transmit analog physiological signals.

16. The interface system of claim 15, wherein the signal converter comprises an analog-to-digital converter and a programmable device, wherein the analog-to-digital converter is configured to receive the analog physiological signals from the wireless signal receiver and to convert the analog physiological signals into digital physiological signals, and wherein the programmable device is configured to process the digital physiological signals and determine a voltage level for mimicking the electrical output from the at least one of the tocodynamometer, the intrauterine pressure catheter, or the fetal scalp electrode.

17. The interface system of claim 16, wherein the signal converter further comprises a digital-to-analog converter configured to receive the voltage level and to convert the voltage level into second analog physiological signals.

18. The interface system of claim 1, wherein the signal converter further comprises a memory configured to store the output data, wherein the signal converter is further configured to transmit on a non-continuous basis the output data stored in the memory to the maternal-fetal monitor via the maternal-fetal monitor port interface.

19. The interface system of claim 1, wherein the sensor array further includes an acoustic sensor configured to detect an acoustic signal.

20. The interface system of claim 19, wherein the plurality of electrodes further includes an electrode configured to detect an electrocardiography signal.

* * * * *